United States Patent

Nohira et al.

[11] Patent Number: 5,830,386
[45] Date of Patent: Nov. 3, 1998

[54] OPTICALLY ACTIVE COMPOUND, LIQUID CRYSTAL COMPOSITION, DEVICE, DISPLAY APPARATUS AND DISPLAY METHOD

[75] Inventors: Hiroyuki Nohira, Urawa; Shinichi Nakamura, Isehara; Ikuo Nakazawa; Koji Noguchi, both of Atsugi, all of Japan

[73] Assignee: Canon Kabushiki Kaisha, Tokyo, Japan

[21] Appl. No.: 669,826

[22] Filed: Jun. 26, 1996

Related U.S. Application Data

[63] Continuation of Ser. No. 193,409, Feb. 7, 1994, abandoned.

[30] Foreign Application Priority Data

Feb. 10, 1993 [JP] Japan .................................. 5-044418

[51] Int. Cl.$^6$ ......................... C09K 19/34; C07D 239/02
[52] U.S. Cl. ...................................... 252/299.61; 544/298
[58] Field of Search ................... 252/299.61; 544/298

[56] References Cited

U.S. PATENT DOCUMENTS

| | | | |
|---|---|---|---|
| 4,367,924 | 1/1983 | Clark et al. ............................ | 359/56 X |
| 4,867,903 | 9/1989 | Nohira et al. ........................ | 252/299.61 |
| 4,873,018 | 10/1989 | Nohira et al. ........................ | 252/299.01 |
| 5,073,306 | 12/1991 | Nohira et al. ........................ | 252/299.61 |
| 5,075,030 | 12/1991 | Togano et al. ........................ | 252/299.61 |
| 5,091,109 | 2/1992 | Takiguchi et al. ................... | 252/299.61 |
| 5,244,595 | 9/1993 | Yamada et al. ...................... | 252/299.61 |
| 5,250,218 | 10/1993 | Mori et al. ............................ | 252/299.61 |
| 5,250,219 | 10/1993 | Mori et al. ............................ | 252/299.61 |
| 5,268,123 | 12/1993 | Mori et al. ............................ | 252/299.61 |
| 5,290,477 | 3/1994 | Kondo et al. ........................ | 252/299.61 |
| 5,393,459 | 2/1995 | Wachtler et al. ................... | 252/299.63 |

FOREIGN PATENT DOCUMENTS

| | | |
|---|---|---|
| 0332025 | 9/1989 | European Pat. Off. . |
| 0352479 | 1/1990 | European Pat. Off. . |
| 0107216 | 8/1981 | Japan . |
| WO 13611 | 11/1990 | WIPO . |

OTHER PUBLICATIONS

Chemistry Letters, The Chemical Society of Japan, No. 7 (1993) 1243–1246.
Schadt, App. Phys. Lett., vol. 18, No. 4 (1971) 127–8.

*Primary Examiner*—C. H. Kelly
*Attorney, Agent, or Firm*—Fitzpatrick, Cella, Harper & Scinto

[57] ABSTRACT

An optically active compound of the formula (I) according to claim 1 is suitable as a component for a liquid crystal composition providing improved response speed. The optically active compound of the formula (I) is characterized by having a fluorine-substituted optically active cite and

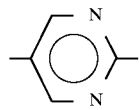

group connected by 1–6 methylene groups. The above liquid crystal composition is useful as an element of a liquid crystal device and a display apparatus providing a good display characteristics.

32 Claims, 4 Drawing Sheets

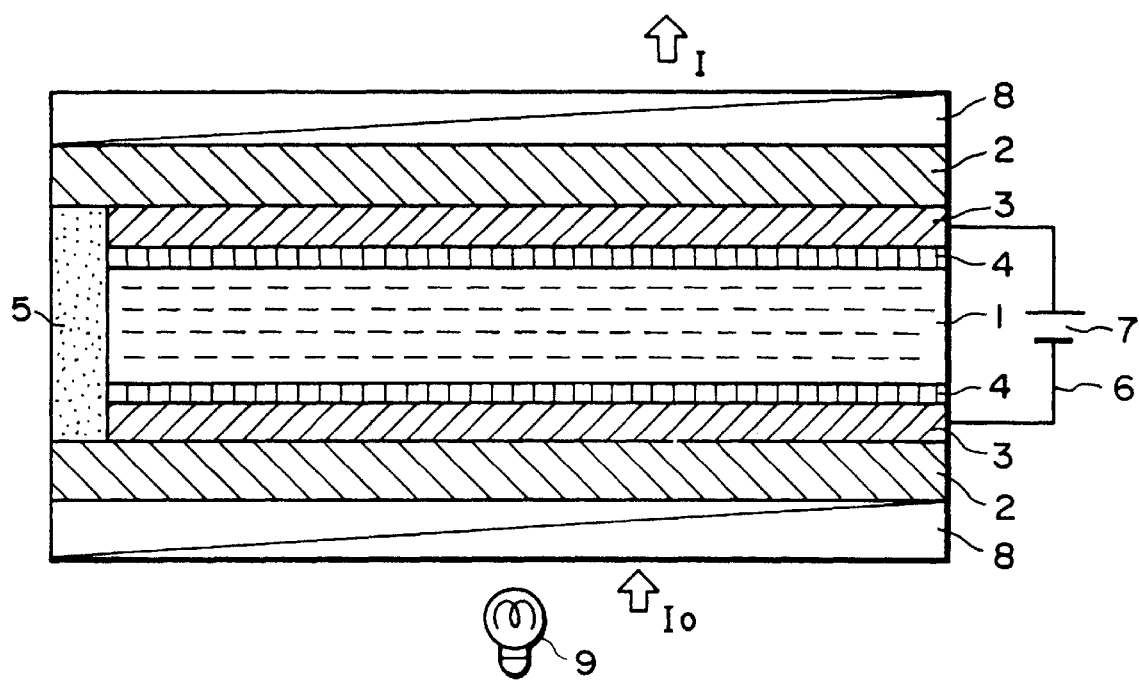
F I G. 1

OPTICALLY ACTIVE COMPOUND, LIQUID CRYSTAL COMPOSITION, DEVICE, DISPLAY APPARATUS AND DISPLAY METHOD

This application is a continuation of application Ser. No. 08/193,409 filed Feb. 7, 1994, now abandoned.

FIELD OF THE INVENTION AND RELATED ART

The present invention relates to an optically active compound, a liquid crystal composition, a liquid crystal device, a display apparatus and a display method, and more particularly to an optically active mesomorphic compound, a liquid crystal composition containing the mesomorphic compound with improved responsiveness to an electric field, a liquid crystal device using the liquid crystal composition for use in a display device, a liquid crystal-optical shutter, etc., a display apparatus using the device, and a display method of using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of μsec, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 107216/1981; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, etc. Among a response time τ, the magnitude of spontaneous polarization Ps and viscosity η, the following relationship exists: $\tau = \eta/(Ps.E)$, where E is an applied voltage. Accordingly, a high response speed can be obtained by (a) increasing the spontaneous polarization Ps, (b) lowering the viscosity η, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°–40° C., the response speed changes by a factor of about 20, so that it actually exceeds the range controllable by driving voltage and frequency.

Thus, as described hereinabove, commercialization of a ferroelectric liquid crystal device requires a liquid crystal composition assuming a chiral smectic phase which has not only a high-speed responsiveness due to a large spontaneous polarization and a low viscosity but also a small temperature-dependence of response speed.

The liquid crystal composition is further required to optimize physical properties such as spontaneous polarization, a helical pitch in a chiral smectic C phase, a helical pitch in a cholesteric phase, a temperature range showing a mesomorphic phase, optical anisotropy, a tilt angle, and dielectric anisotropy in order to realize good characteristics including a uniform switching during display, a good visual angle characteristic, improved low temperature storage properties and alleviation of load imposed on driving IC.

SUMMARY OF THE INVENTION

An object of the present invention is to provide a mesomorphic compound effective for providing high response speed, a liquid crystal composition containing the mesomorphic compound for providing a practical ferroelectric liquid crystal device as described above, a liquid crystal device including the liquid crystal composition, a display apparatus including the device, and a display method of using the composition or device.

According to the present invention, there is provided an optically active compound represented by the following formula (I):

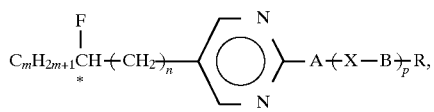 (I)

wherein R denotes a linear or branched alkyl group having 1–18 carbon atoms capable of including one or non-neighboring two or more methylene groups which can be replaced with —O—, —S—, —CO—, —COO—, —OCO—, —CH=CH— or —C≡C—, said alkyl group capable of including hydrogen which can be replaced with fluorine; X denotes a single bond, —COO—, —OCO—, —CH$_2$O—, —OCH$_2$—, —CH$_2$CH$_2$—or —C≡C—; A denotes

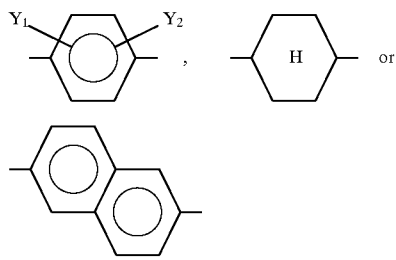

wherein Y$_1$ and Y$_2$ independently denote hydrogen, fluorine, methyl or trifluoromethyl; B denotes A,

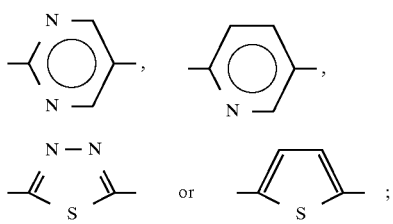

m is an integer of 1–16; n is an integer of 1–6; p is 0 or 1; and * denotes the location of an optically active center.

According to the present invention, there is also provided a liquid crystal composition containing at least one species of the above-mentioned optically active compound of the formula (I).

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method of using the liquid crystal composition or the liquid crystal device described above and switching the alignment direction of liquid crystal molecules by applying voltages to the liquid crystal composition to effect display.

This and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1 is a schematic sectional view of a liquid crystal display device using a liquid crystal composition assuming a chiral smectic phase;

DETAILED DESCRIPTION OF THE INVENTION

Figure 2:
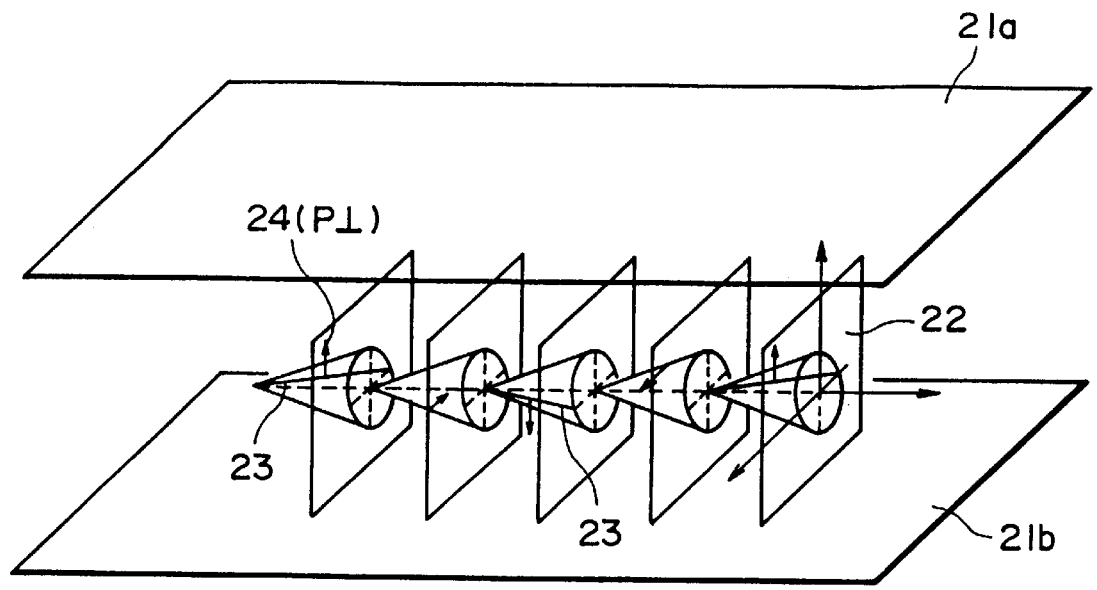
FIGS. 2 and 3 are schematic perspective views an embodiment of a device cell for illustrating the operation principle of a liquid crystal device utilizing ferroelectricity of a liquid crystal composition.

Preferred examples of the optically active compound of the formula (I) may include those containing

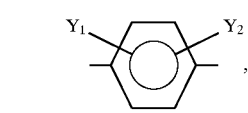

wherein Y$_1$ and Y$_2$ are the same as in the formula (I), as A in the formula (I) in view of improvements in a mesomorphic temperature range, compatibility, alignment characteristic, easiness of synthesis, etc.

In view of viscosity, preferred examples of the optically active compound of the formula (I) may include those of the following formulae (Ia) and (Ib) having a single bond as X:

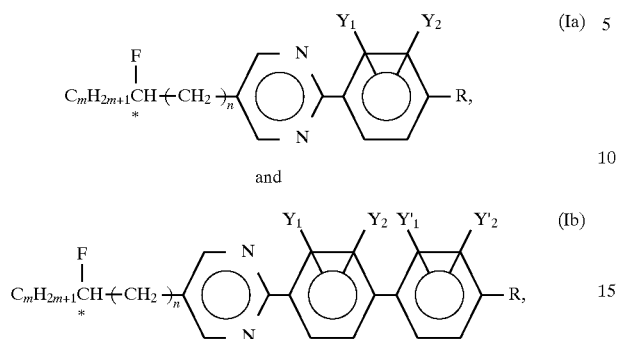

wherein R, m, n, $Y_1$, $Y_2$ and the symbol * have the same meanings as defined above; and $Y'_1$ and $Y'_2$ independently denote H, F, $CH_3$, or $CF_3$.

In order to obtain larger spontaneous polarization, n in the formula (I) may preferably be 1 or 2.

Preferred examples of R of the formula (I) may include those of the following groups (i) to (v):

$$n\text{-}C_aH_{2a+1}-Z- \quad \text{(i)}$$

$$C_bH_{2b+1}\overset{CH_3}{\underset{|}{CH}}(CH_2)_d Z- \quad \text{(ii)}$$

$$C_eH_{2e+1}O(CH_2)_f\overset{CH_3}{\underset{|}{CH}}(CH_2)_g Z- \quad \text{(iii)}$$

$$C_hH_{2h+1}\overset{F}{\underset{|}{CH}}(CH_2)_i Z- \quad \text{(iv)}$$

$$C_jF_{2j+1}(CH_2)_k Z- \quad \text{(v)}$$

wherein a and j independently denote an integer of 1–16; and e independently denote an integer of 1–8; f and i independently denote 0 or 1; d, g and k independently denote an integer of 0–7; h is an integer of 1–15; and Z is a single bond, —O—, —COO— or —OCO—.

The optically active (mesomorphic) compound of the above-mentioned formula (I) may preferably be synthesized through the following reaction schemes.

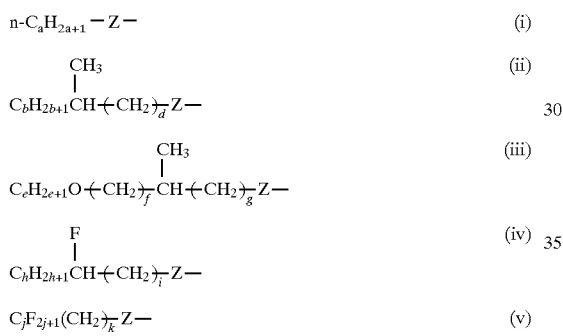

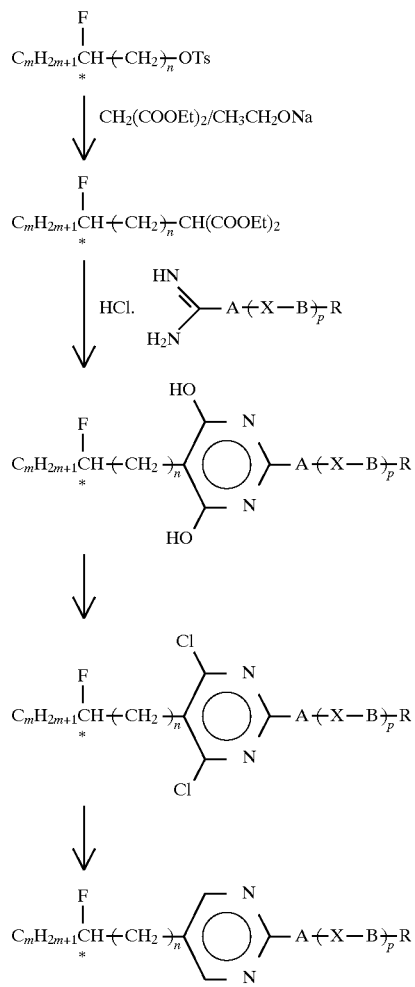

In the above, m, n, R, A, B, X and p are the same as in the above-mentioned formula (I).

Specific examples of the optically active compound represented by the formula (I) may include those shown by the following structural formulas.

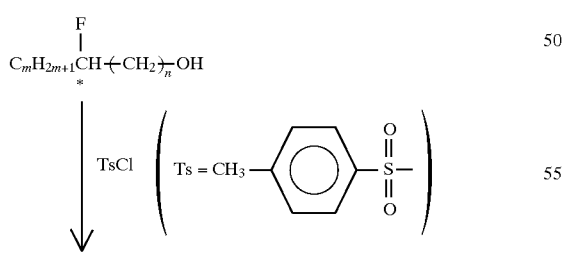

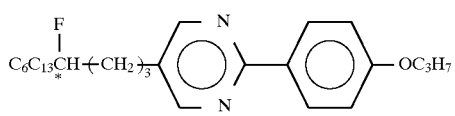

(1)

-continued
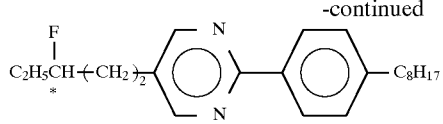 (2)
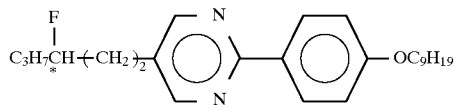 (3)
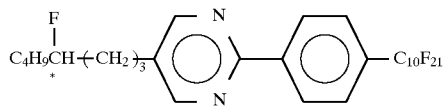 (4)
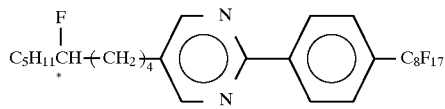 (5)
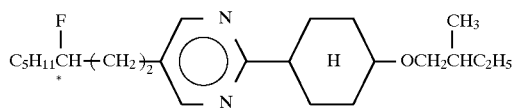 (6)
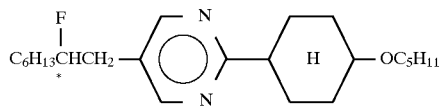 (7)
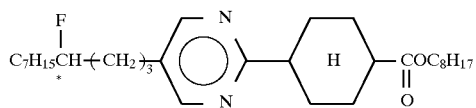 (8)
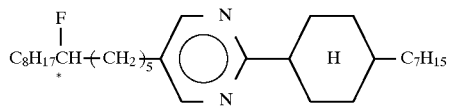 (9)
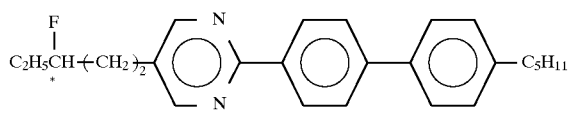 (10)
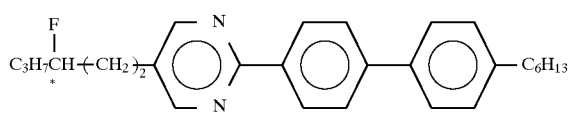 (11)
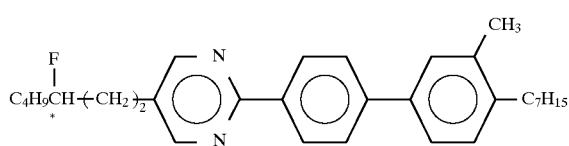 (12)
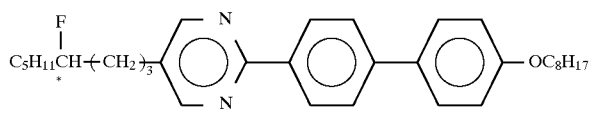 (13)
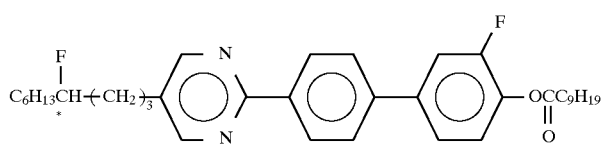 (14)

-continued
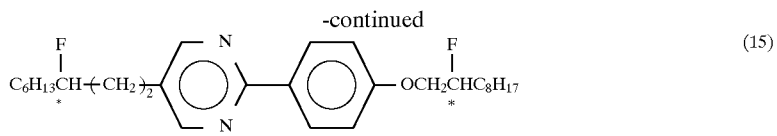 (15)
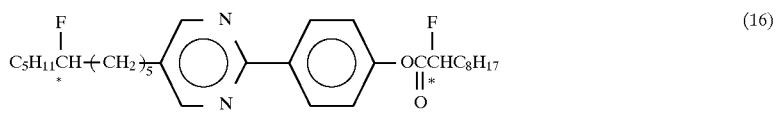 (16)
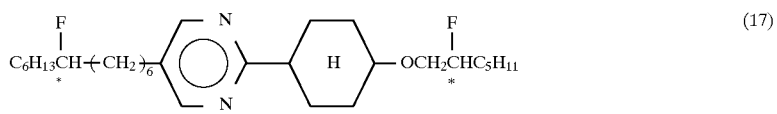 (17)
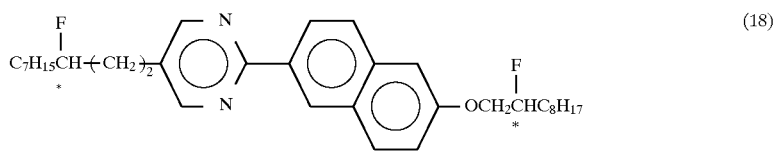 (18)
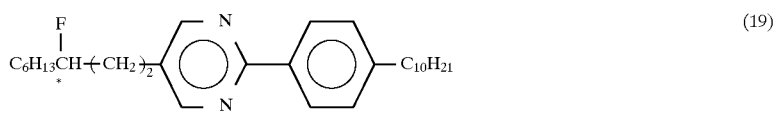 (19)
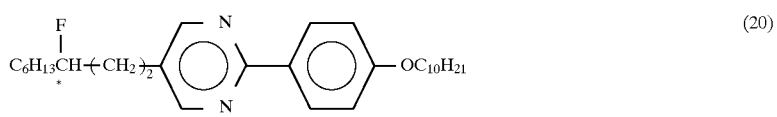 (20)
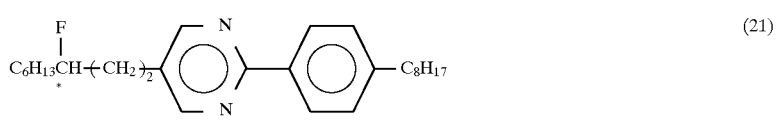 (21)
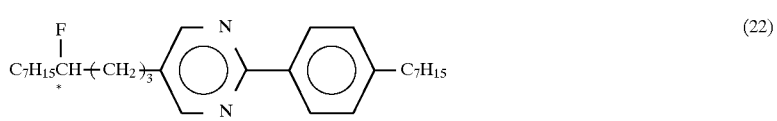 (22)
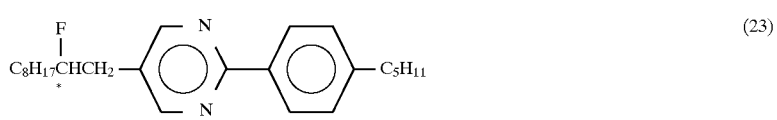 (23)
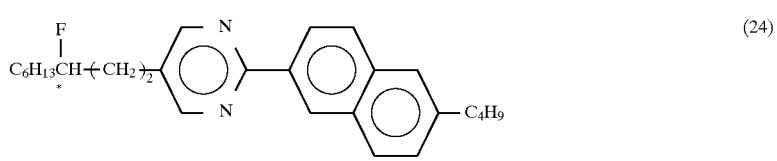 (24)
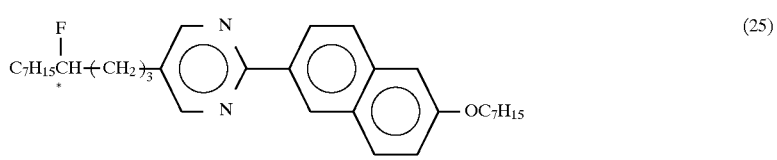 (25)
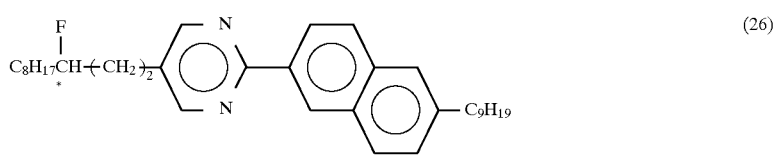 (26)

-continued
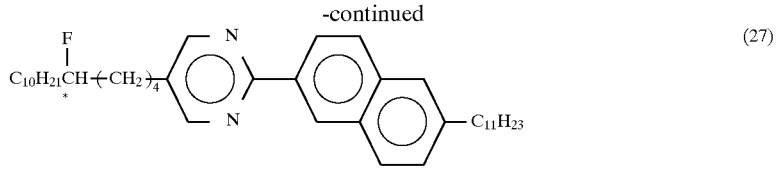
(27)
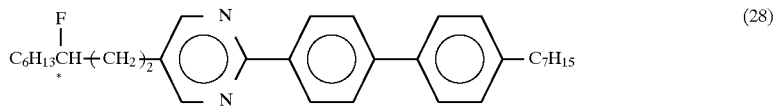
(28)
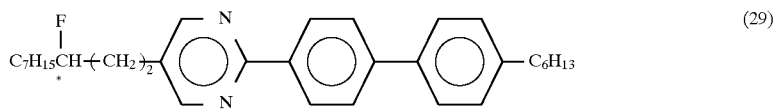
(29)
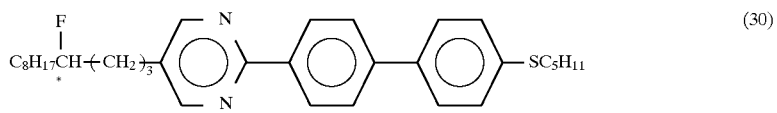
(30)
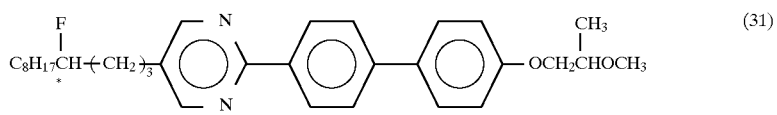
(31)
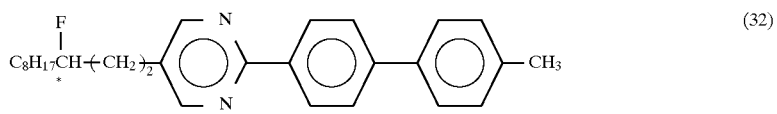
(32)
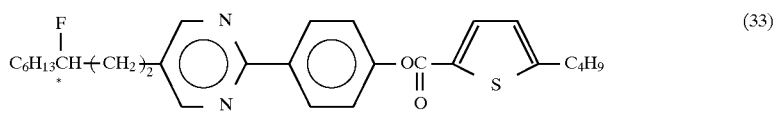
(33)
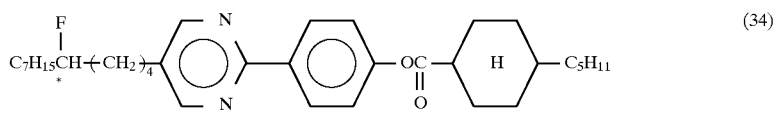
(34)
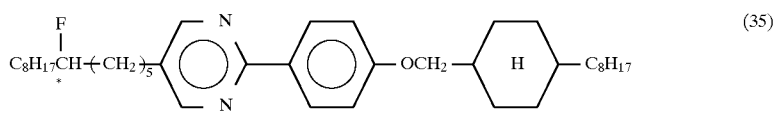
(35)
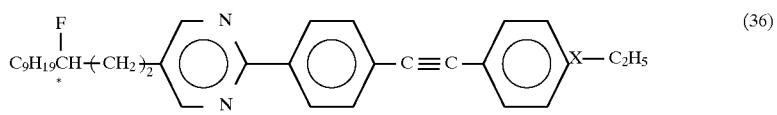
(36)
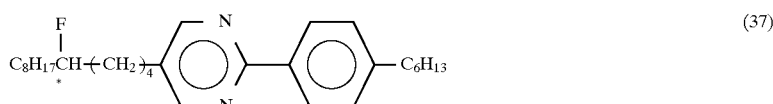
(37)
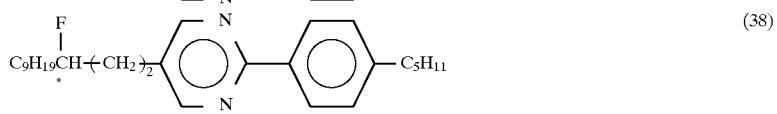
(38)
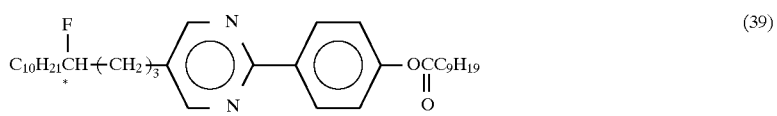
(39)

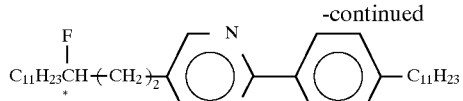 (40)
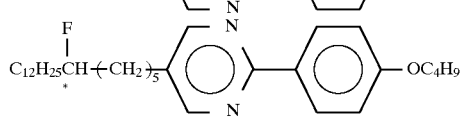 (41)
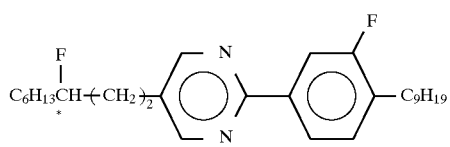 (42)
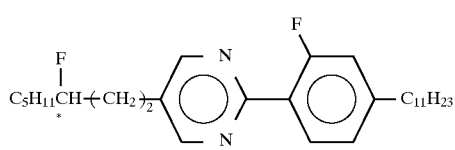 (43)
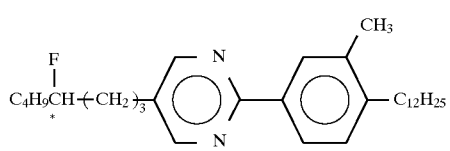 (44)
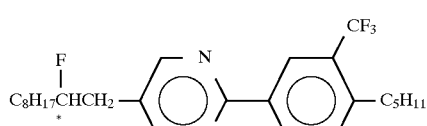 (45)
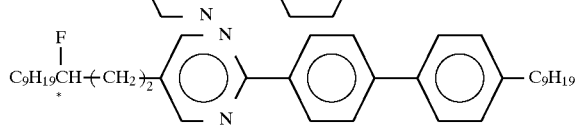 (46)
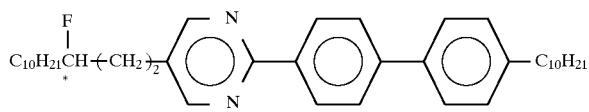 (47)
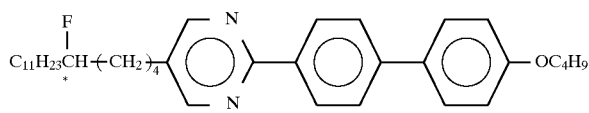 (48)
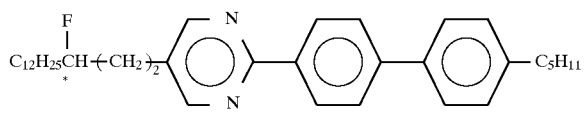 (49)
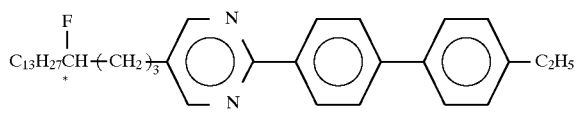 (50)
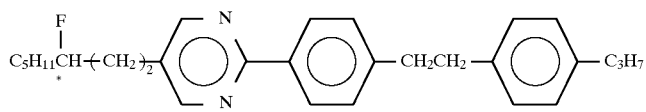 (51)
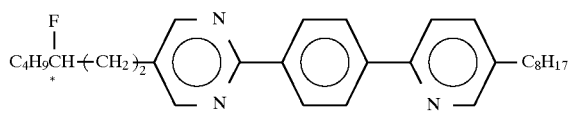 (52)

-continued
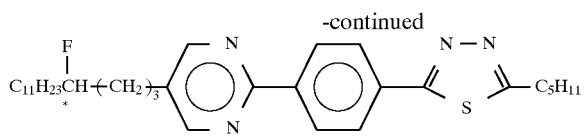 (53)
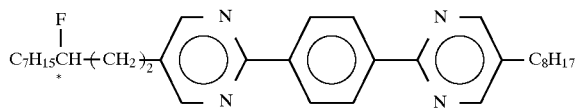 (54)
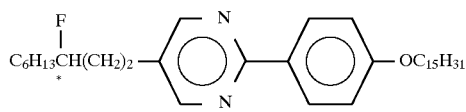 (55)
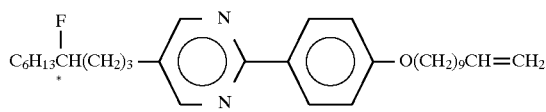 (56)
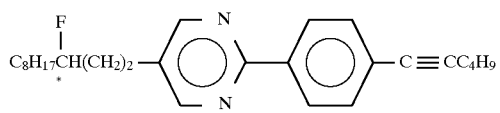 (57)
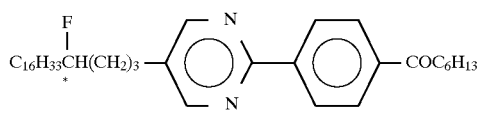 (58)
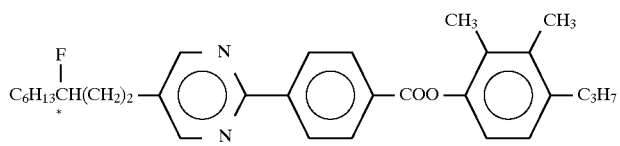 (59)
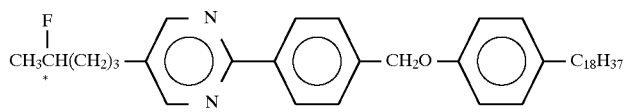 (60)
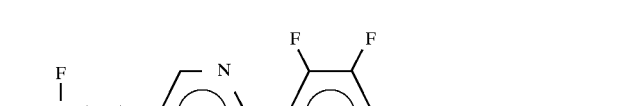 (61)
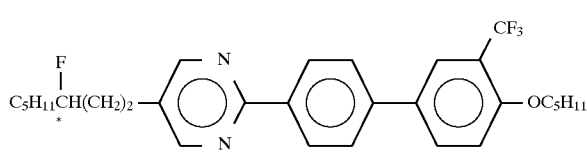 (62)
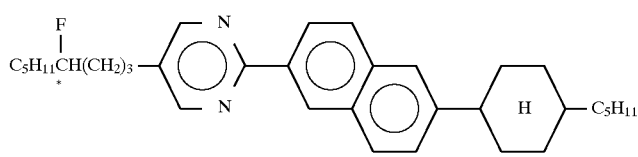 (63)
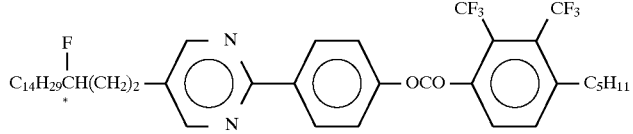 (64)

-continued

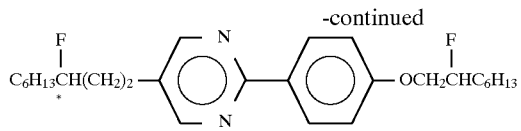
(65)

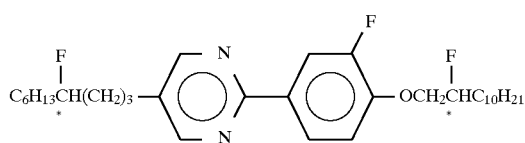
(66)

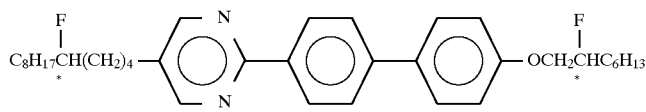
(67)

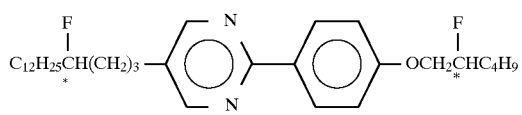
(68)

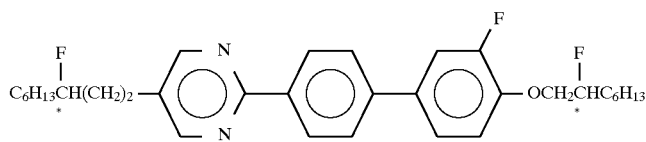
(69)

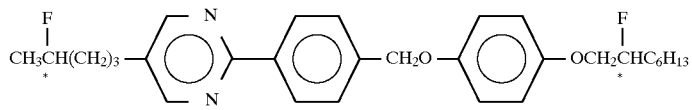
(70)

The liquid crystal composition according to the present invention may be obtained by mixing at least one species of the optically active compound represented by the formula (I) and at least one species of another mesomorphic compound in appropriate proportions.

The liquid crystal composition according to the present invention may preferably be formulated as a liquid crystal composition capable of showing ferroelectricity, particularly a liquid crystal composition showing a chiral smectic phase.

Specific examples of another mesomorphic compound described above may include those denoted by the following formulas (III) to (XIII).

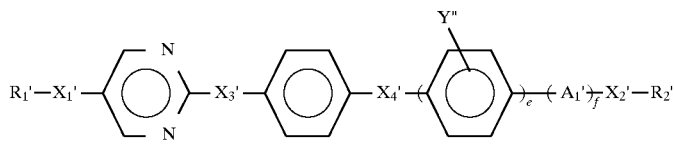
(III)

wherein e denotes 0 or 1 and f denotes 0 or 1 with proviso that e+f=0 or 1; YΔ denotes H, halogen, $CH_3$ or $CF_3$; $X_1'$ and $X_2'$ respectively denote a single bond,

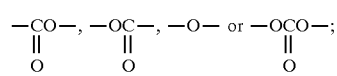

$X_3'$ and $X_4'$ respectively denote a single bond, $$-\underset{\underset{O}{\|}}{C}O-,\ -O\underset{\underset{O}{\|}}{C}-,$$

$-OCH_2-$ or $-CH_2O-$; and $A_1'$ denotes

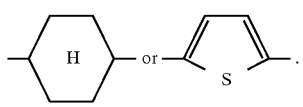

In the formula (III), preferred compounds thereof may include those represented by the following formulas (IIIa) to (IIIe):

(IIIa)
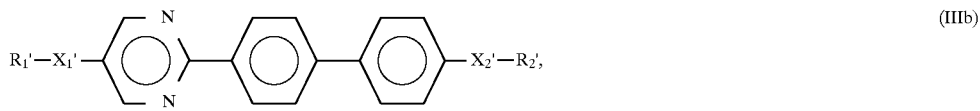
(IIIb)
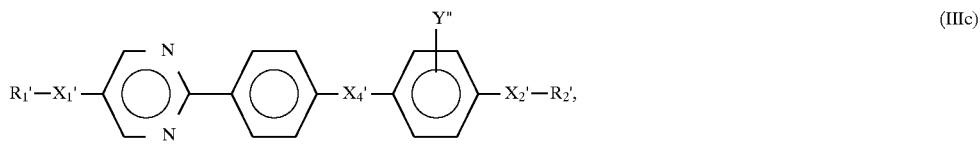
(IIIc)
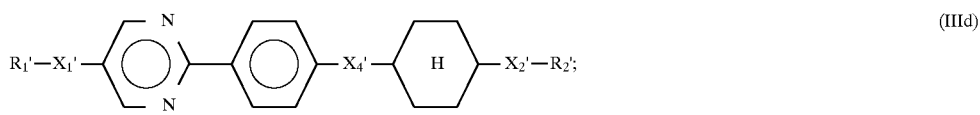
(IIId)
and
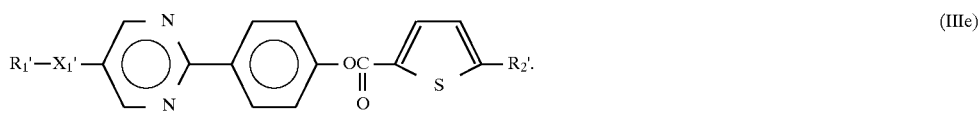
(IIIe)
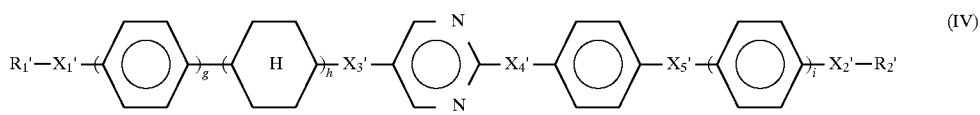
(IV)
wherein g and h respectively denote 0 or 1 with proviso that g+h=1; i denotes 0 or 1; $X_1'$ and $X_2'$ respectively denote a single bond,
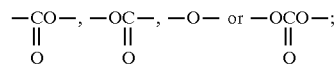
and $X_3'$, $X_4'$ and $X_5'$ respectively denote a single bond,
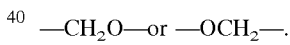
—CH$_2$O— or —OCH$_2$—.
In the formula (IV), preferred compounds thereof may include those represented by the following formulas (IVa) to (IVc):
(IVa)
(IVb)
and
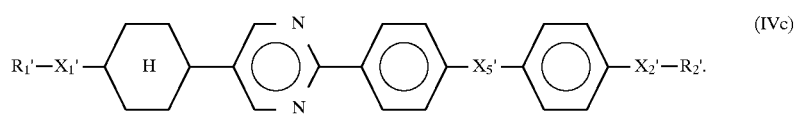
(IVc)

-continued

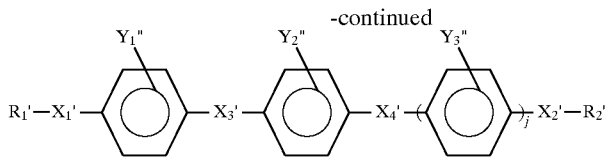

wherein j denotes 0 or 1; $Y_1''$, $Y_2''$ and $Y_3''$ respectively denote H, halogen, $CH_3$ or $CF_3$; $X_1'$ and $X_2'$ respectively denote a single bond,

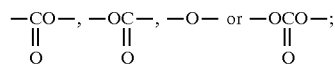

and $X_3'$ and $X_4'$ respectively denote a single bond,

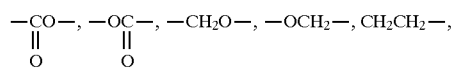

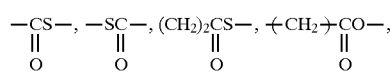

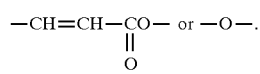

In the formula (V), preferred compounds thereof may include those represented by the following formulas (Va) and (Vb):

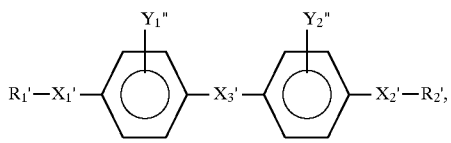

and

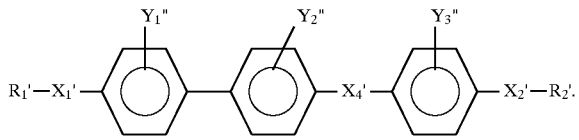

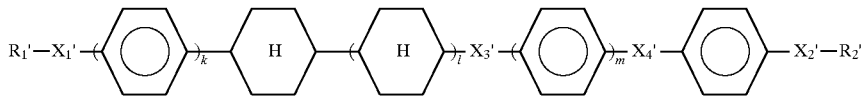

wherein k, l and m respectively denote 0 or 1 with proviso that k+l+m=0, 1 or 2; $X_1'$ and $X_2'$ respectively denote a single bond,

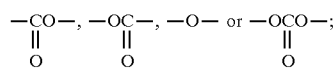

and $X_3'$ and $X_4'$ respectively denote a single bond,

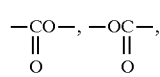

—$CH_2O$— or —$OCH_2$—.

In the formula (VI), preferred compounds thereof may include those represented by the following formulas (VIa) to (VIf):

 (V)

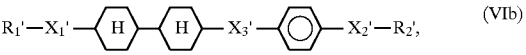 (VIa)

 (VIb)

 (VIc)

 (VId)

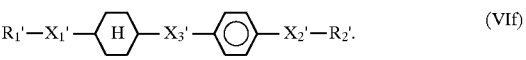 (VIe)

and (VIf)

Herein, $R_1'$ and $R_2'$ respectively denote a linear or branched alkyl group having 1–18 carbon atoms capable of including one or non-neighboring two or more methylene groups which can be replaced with —CH halogen- and (Va)

(Vb)

(VI)

capable of further including one or two or more non-neighboring methylene groups other than those directly connected to $X_1'$ or $X_2'$ which can be replaced with at least one species of —O—,

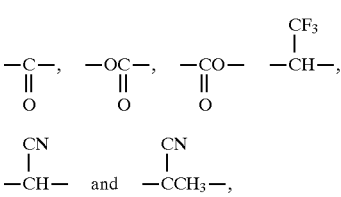

with proviso that $R_1'$ and $R_2'$ respectively do not connect to a ring structure by a single bond when $R_1'$ and $R_2'$ respectively denote a halogenated alkyl group containing one methylene group replaced with —CH halogen- or —CH($CF_3$)—.

Further, preferred examples of $R_1'$ and $R_2'$ may respectively include those represented by the following groups (i) to (xi):

i) a linear alkyl group having 1–15 carbon atoms;

ii) $-(CH_2)_{p}-\overset{CH_3}{\underset{|}{CH}}-C_qH_{2q+1}$ wherein p denotes an integer of 0–5 and q denotes an integer of 2–11 (optically active or inactive);

iii) $-(CH_2)_{r}-\overset{CH_3}{\underset{|}{CH}}-(CH_2)_{s}-OC_tH_{2t+1}$ wherein r denotes an integer of 0–6, s denotes 0 or 1, and t denotes an integer of 1–14 (optically active or inactive);

iv) $-(CH_2)_{u}-\overset{F}{\underset{|}{\overset{*}{CH}}}-C_vH_{2v+1}$ wherein u denotes 0 or 1 and v denotes an integer of 1–16;

v) $-\overset{CH_3}{\underset{|}{CH}}CO C_wH_{2w+1}$
$\phantom{-CHCOC_wH}\|$
$\phantom{-CHCOC_wH}O$ wherein w denotes an integer of 1–15 (optically active or inactive);

vi) $-(CH_2)_{x}-\overset{CF_3}{\underset{|}{CH}}-C_yH_{2y+1}$ wherein x denotes an integer of 0–2 and y denotes an integer of 1–15 (optically active or inactive).

vii) $-\overset{CF_3}{\underset{|}{\overset{*}{CH}}}CH_2COC_zH_{2z+1}$
$\phantom{-CHCH_2CO}\|$
$\phantom{-CHCH_2CO}O$ wherein z denotes an integer of 1–15.

viii) $-(CH_2)_{A}-\overset{CN}{\underset{|}{CH}}-C_BH_{2B+1}$ wherein A denotes an integer of 0–2 and B denotes an integer of 1–15 (optically active or inactive);

ix) $-(CH_2)_{C}-\overset{CN}{\underset{|}{\underset{CH_3}{C}}}-C_DH_{2D+1}$ wherein C denotes an integer of 0–2 and D denotes an integer of 1–15 (optically active or inactive).

x) hydrogen (H), and xi) fluorine (F).

In the above-mentioned formulas (IIIa) to (IIId), more preferred compounds thereof may include those represented by the formulas (IIIaa) to (IIIdc):

$R_1'-\underset{N}{\overset{N}{\bigcirc}}-\bigcirc-O-R_2'$ (IIIaa)

$R_1'-\underset{N}{\overset{N}{\bigcirc}}-\bigcirc-O\underset{\|}{C}-R_2'$ (IIIab)
$\phantom{R_1'-\bigcirc-\bigcirc-OC}O$ $R_1'-\underset{N}{\overset{N}{\bigcirc}}-\bigcirc-\underset{\|}{C}O-R_2'$ (IIIac)
$\phantom{R_1'-\bigcirc-\bigcirc-CO}O$ $R_1'O-\underset{N}{\overset{N}{\bigcirc}}-\bigcirc-O-R_2'$ (IIIad)

$R_1'-\underset{N}{\overset{N}{\bigcirc}}-\bigcirc-\bigcirc-R_2'$ (IIIba)

$R_1'-\underset{N}{\overset{N}{\bigcirc}}-\bigcirc-\bigcirc-O-R_2'$ (IIIbb)

$R_1'-\underset{N}{\overset{N}{\bigcirc}}-\bigcirc-\bigcirc-O\underset{\|}{C}-R_2'$ (IIIbc)
$\phantom{xxxxxxxxxxxxxxxxxx}O$ $R_1'O-\underset{N}{\overset{N}{\bigcirc}}-\bigcirc-\bigcirc-R_2'$ (IIIbd)

$R_1'-\underset{N}{\overset{N}{\bigcirc}}-\bigcirc-O\underset{\|}{C}-\overset{Y''}{\bigcirc}-R_2'$ (IIIca)
$\phantom{xxxxxxxxxxxxxx}O$ $R_1'-\underset{N}{\overset{N}{\bigcirc}}-\bigcirc-OCH_2-\overset{Y''}{\bigcirc}-R_2'$ (IIIcb)

$R_1'-\underset{N}{\overset{N}{\bigcirc}}-\bigcirc-CH_2O-\overset{Y''}{\bigcirc}-R_2'$ (IIIcc)

$R_1'-\underset{N}{\overset{N}{\bigcirc}}-\bigcirc-\underset{\|}{C}O-\overset{Y''}{\bigcirc}-R_2'$ (IIIcd)
$\phantom{xxxxxxxxxxxxxx}O$

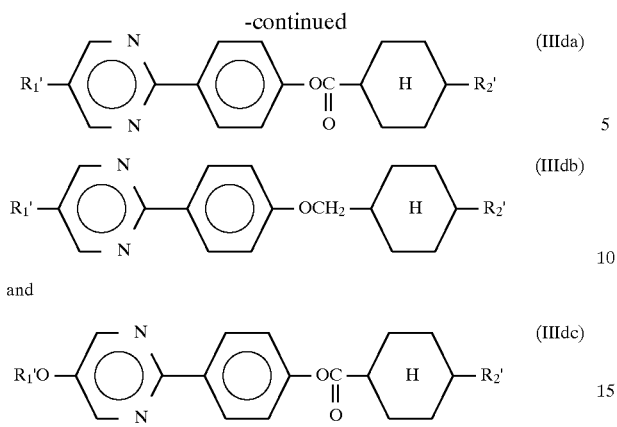
In the above-mentioned formulas (IVa) to (IVc), more preferred compounds thereof may include those represented by the formulas (IVaa) to (IVcd):
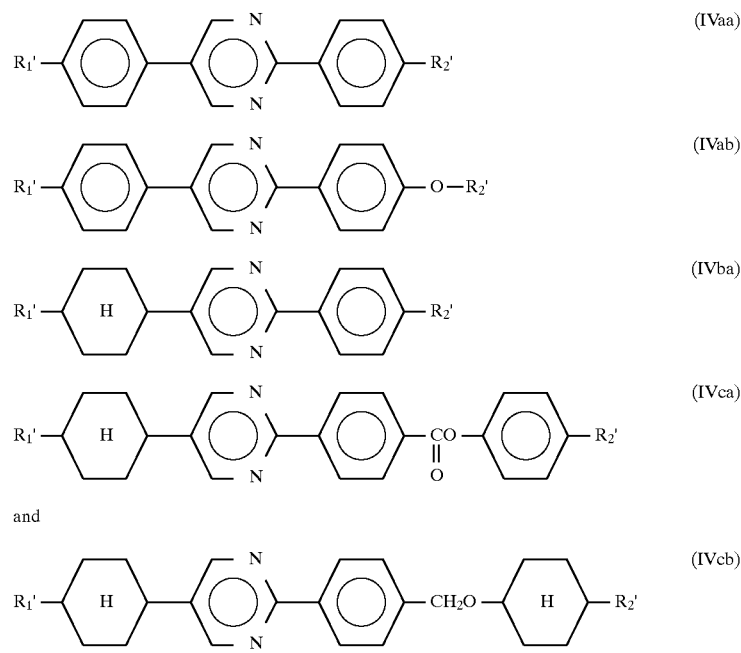
In the above-mentioned formulas (Va) to (Vd), more preferred compounds thereof may include those represented by the formulas (Vaa) to (Vbf):
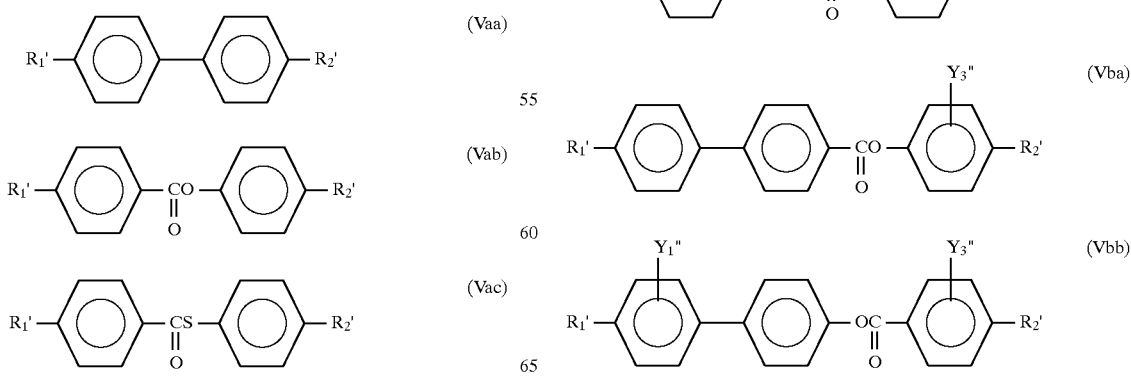

-continued

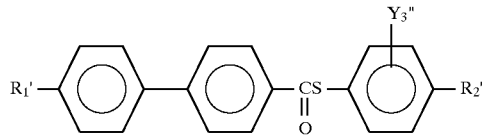 (Vbc)

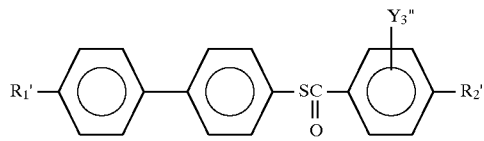 (Vbd)

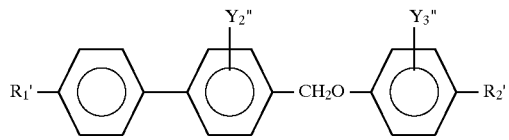 (Vbe)

and

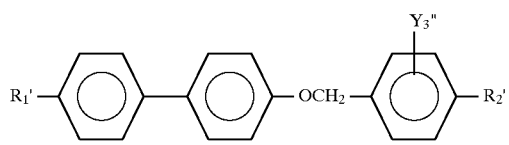 (Vbf)

In the above-mentioned formulas (VIa) to (VIf), more preferred compounds thereof may include those represented by the formulas (VIaa) to (VIfa):

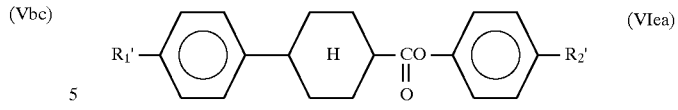 (VIaa)

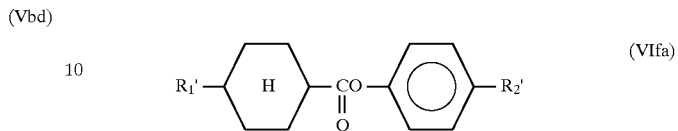 (VIab)

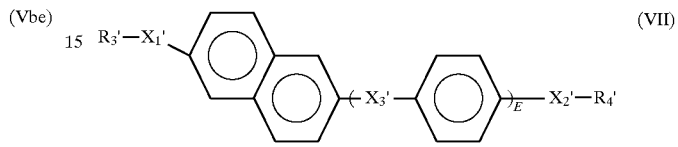 (VIba)

(VIbb)

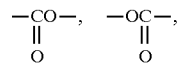 (VIda)

-continued

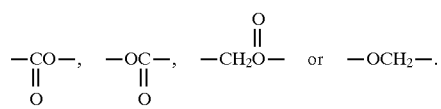 (VIea)

and

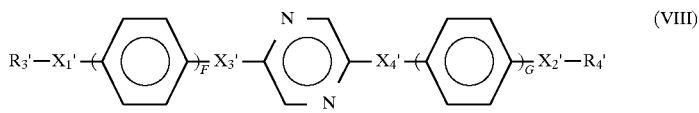 (VIfa)

(VII)

wherein E denotes 0 or 1; $X_1'$ and $X_2'$ respectively denote a single bond, $$-\underset{\underset{O}{\|}}{C}O-, \quad -O\underset{\underset{O}{\|}}{C}-,$$

—O— or —OCO—; and $X_3'$ denotes a single bond, $$-\underset{\underset{O}{\|}}{C}O-, \quad -O\underset{\underset{O}{\|}}{C}-, \quad -CH_2\overset{\overset{O}{\|}}{O}- \quad \text{or} \quad -OCH_2-.$$

(VIII)

wherein F and G respectively denote 0 or 1; $X_1'$ and $X_2'$ respectively denote a single bond, $$-\underset{\underset{O}{\|}}{C}O-, \quad -O\underset{\underset{O}{\|}}{C}-,$$

or —O—; and $X_3'$ and $X_4'$ respectively denote a single bond, $$-\underset{\underset{O}{\|}}{C}O-, \quad -O\underset{\underset{O}{\|}}{C}-,$$

—CH₂O— or —OCH₂—.

In the above formula (VII), preferred compounds thereof may include those represented by the 20 following formulas (VIIa) and (VIIb):

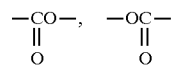 (VIIa)

, and

-continued

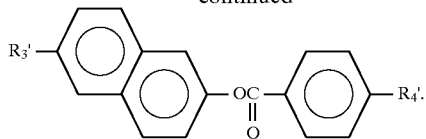
(VIIb)

In the above formula (VIII), preferred compounds thereof may include those represented by the following formulas (VIIIa) and (VIIIb).

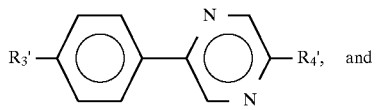
(VIIIa)

and

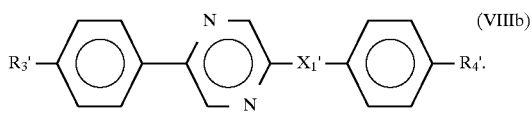
(VIIIb)

More preferred compounds of the formula (VIIIb) may include those represented by the formulas (VIIIba) to (VIIIbb):

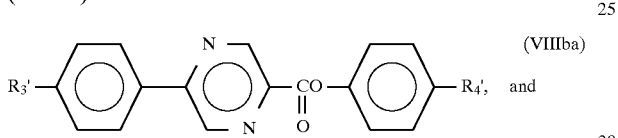
(VIIIba)

and

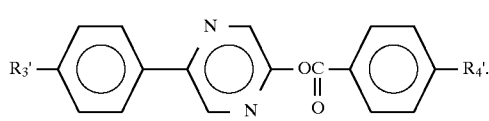
(VIIIbb)

Herein, $R_3'$ and $R_4'$ respectively denote a linear or branched alkyl group having 1–18 carbon atoms capable of including one or non-neighboring two or more methylene groups which can be replaced with —CH halogen- and capable of further including one or two or more non-neighboring methylene groups other than those directly connected to $X_1'$ or $X_2'$ which can be replaced with at least one species of —O—, $$-\underset{O}{\overset{\|}{C}}-, \quad -\underset{O}{\overset{\|}{OC}}-, \quad -\underset{O}{\overset{\|}{CO}}- \quad -\underset{|}{\overset{CN}{CH}}- \quad \text{and} \quad -\underset{|}{\overset{CN}{CCH_3}}-,$$

with proviso that $R_3'$ and $R_4'$ respectively do not connect to a ring structure by a single bond when $R_3'$ and $R_4'$ respectively denote a halogenated alkyl group containing one methylene group replaced with —CH halogen-.

Further, preferred examples of $R_3'$ and $R_4'$ may respectively include those represented by the following groups (i) to (vii):

i) a linear alkyl group having 1–15 carbon atoms;

ii) 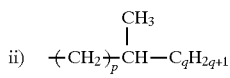

wherein p denotes an integer of 0–5 and q denotes an integer of 2–11 (optically active or inactive);

iii) 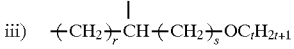

wherein r denotes an integer of 0–6, s denotes 0 or 1, and t denotes an integer of 1–14 (optically active or inactive);

iv) 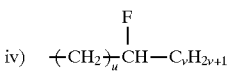

wherein u denotes an integer of 0 or 1 and v denotes an integer of 1–16 (optically active or inactive);

v) 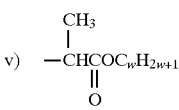

wherein w denotes an integer of 1–15 (optically active or inactive);

vi) 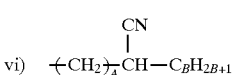

wherein A denotes an integer of 0–2 and B denotes an integer of 1–15 (optically active or inactive); and vii) 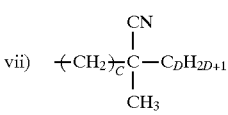

wherein C denotes an integer of 0–2 and D denotes an integer of 1–15 (optically active or inactive).

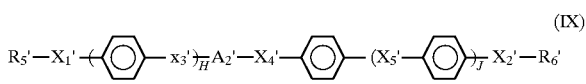
(IX)

wherein H and J respectively denote 0 or 1 with proviso that H+J=0 or 1; $X_1'$ and $X_2'$ respectively denote a single bond, $$-\underset{O}{\overset{\|}{CO}}-, \quad -\underset{O}{\overset{\|}{OC}}-$$

or —O—; $A_2'$ denotes

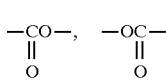

and $X_3'$ and $X_4'$ respectively denote a single bond, $$-\underset{O}{\overset{\|}{CO}}-, \quad -\underset{O}{\overset{\|}{OC}}-, \quad -CH_2O- \quad \text{or} \quad -OCH_2-.$$

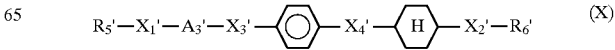
(X)

wherein $X_1'$ and $X_2'$ respectively denote a single bond,

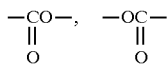

or —O—; $A_3'$ denotes

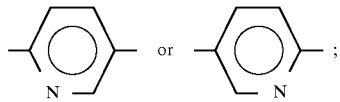

and $X_3'$ and $X_4'$ respectively denote a single bond,

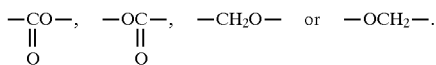

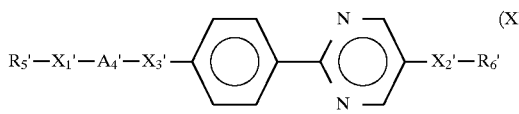            (XI)

wherein $X_1'$ and $X_2'$ respectively denote a single bond,

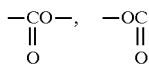

or —O—; $A_4'$ denotes

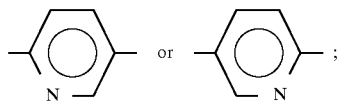

and $X_3'$ respectively denotes a single bond,

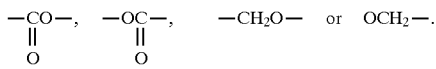

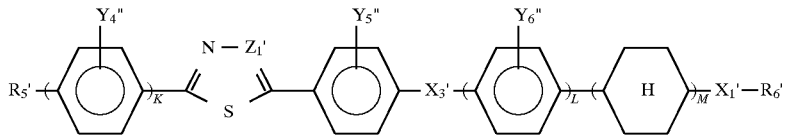

wherein K, L and M respectively denote 0 or 1 with the proviso that K+L+M=0 or 1 ; $X_1'$ denotes a single bond,

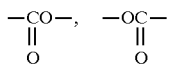

or —O—; $X_3'$ denotes a single bond,

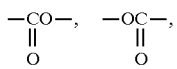

—CH 2O—or —OCH$_2$—; $Y_4''$, $Y_5''$ and $Y_6''$ respectively denote H or F; and $Z_1'$ is CH or N.

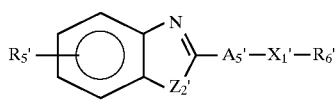            (XIII)

wherein $Z_2'$ denotes —O—or —S—; and $A_5'$ denotes

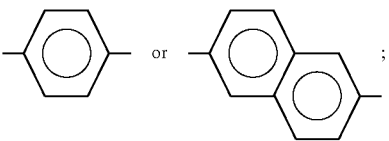

$X_1'$ denotes a single bond,

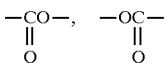

or —O—.

In the above formula (IX), preferred compounds thereof may include those represented by the following formulas (IXa) to (IXc):

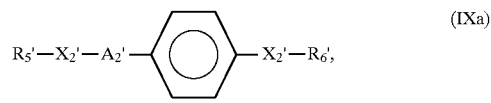            (IXa)

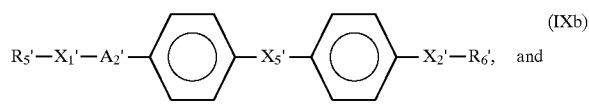            (IXb)

and

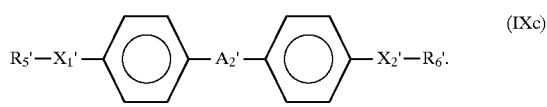            (IXc)

In the above formula (X), preferred compounds thereof may include those represented by the following formulas (Xa) and (Xb):

            (XII)

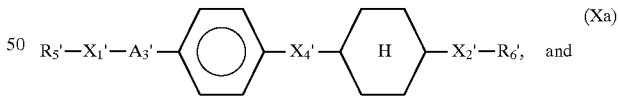            (Xa)

and

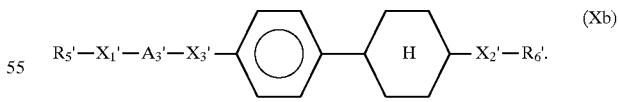            (Xb)

In the above formula (XII), preferred compounds thereof may include those represented by the following formulas (XIIa) and (XIIf):

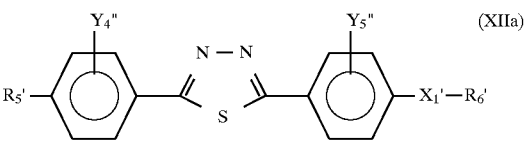            (XIIa)

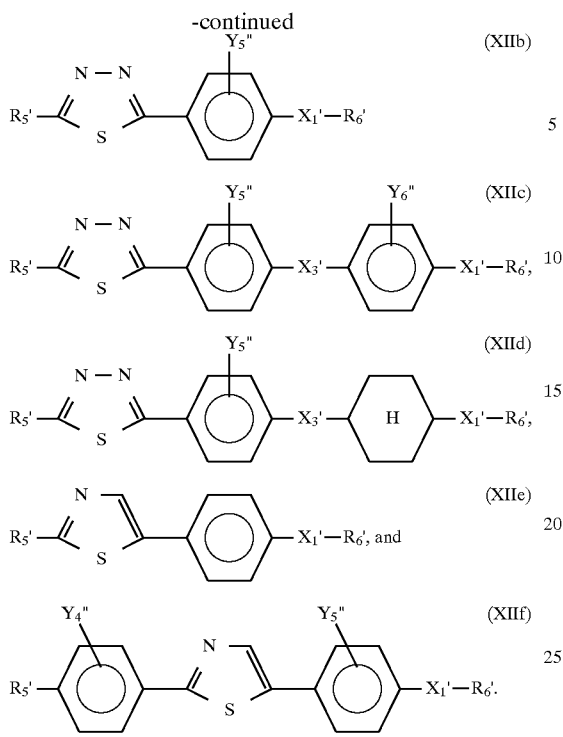

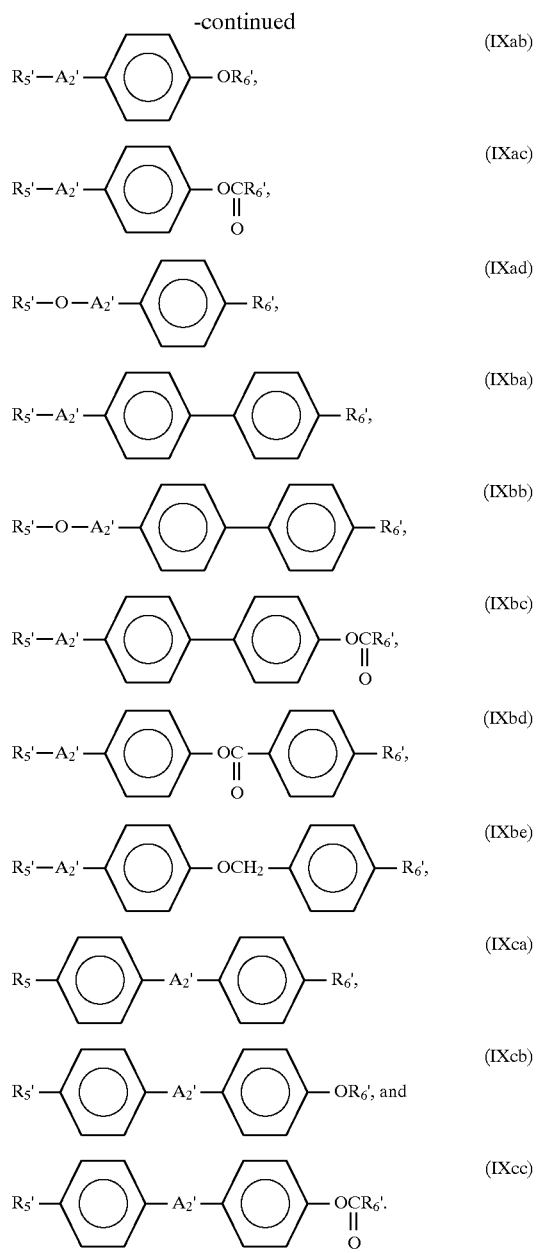

In the above formula (XIII), preferred compounds thereof may include those represented by the following formulas (XIIIa) to (XIIIe):

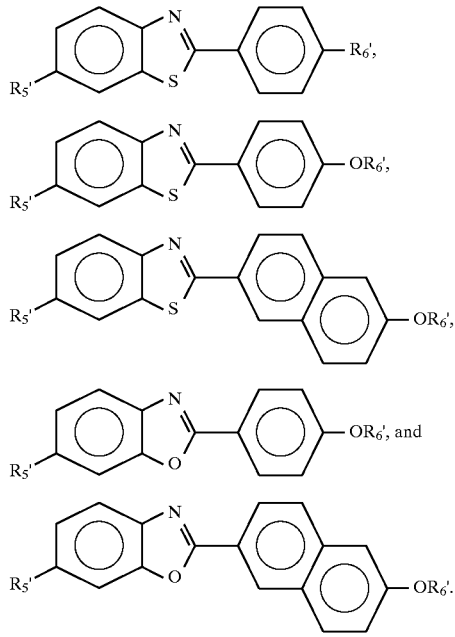

In the above-mentioned formulas (IXa) to (IXc), more preferred compounds thereof may include those represented by the formulas (IXaa) to (IXcc):

In the above-mentioned formulas (Xa) to (Xb), more preferred compounds thereof may include those represented by the formulas (Xaa) to (Xbb):

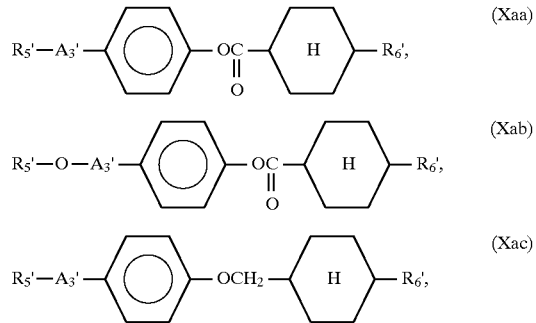

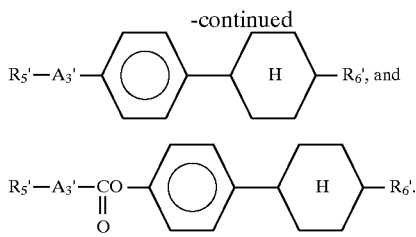(Xba)

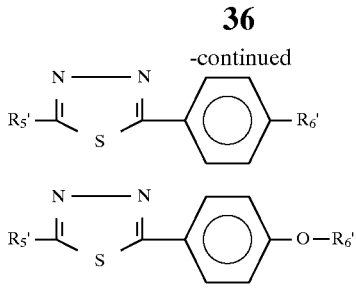(XIIba)

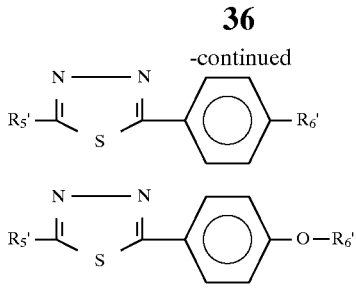

(Xbb)

(XIIbb)

(XIIbc)

In the above formula (XI), preferred compounds thereof may include those represented by the following formulas (XIa) to (XIg):

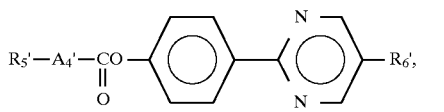(XIa)

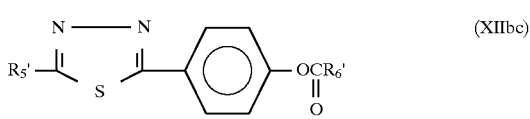(XIca)

(XIb)

(XIcb)

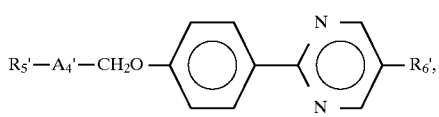(XIc)

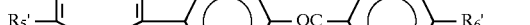(XIIda)

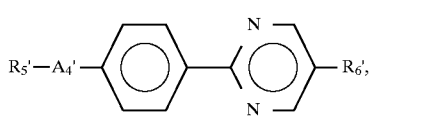(XId)

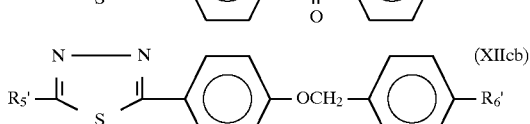(XIIdb)

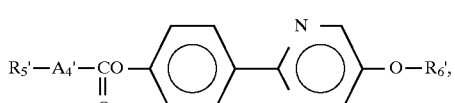(XIe)

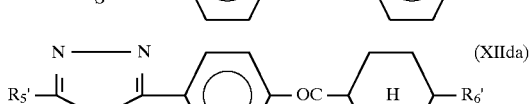(XIIea)

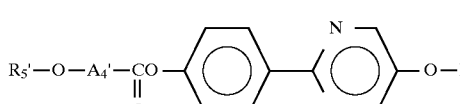(XIf)

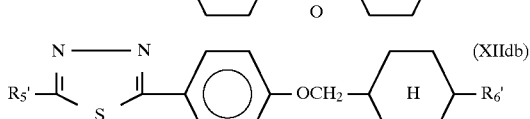(XIIfa)

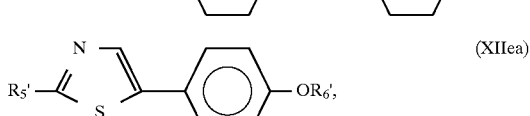(XIIfb)

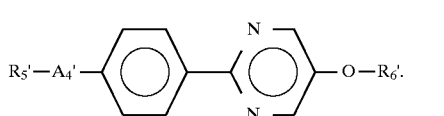(XIg)

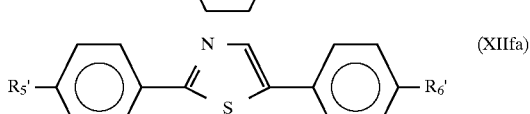(XIIfc)

In the above-mentioned formulas (XIIa) to (XIIf), more preferred compounds thereof may include those represented by the formula (XIIaa) to (XIIfc):

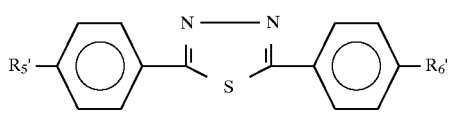(XIIaa)

Herein, $R_5'$ and $R_6'$ respectively denote a linear or branched alkyl group having 1–18 carbon atoms capable of including one non-neighboring two or more methylene groups other than those directly connected to $X_1'$ or $X_2'$ which can be replaced with at least one species of —O—,

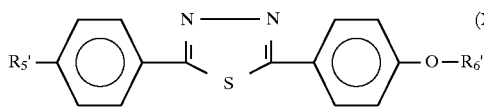(XIIab)

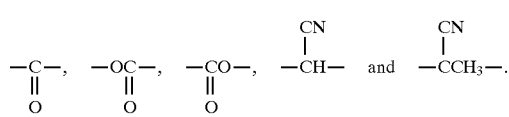

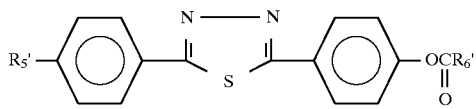(XIIac)

Further, preferred examples of $R_5'$ and $R_6'$ may respectively include those represented by the following groups (i) to (vi):

i) a linear alkyl group having 1–15 carbon atoms;

ii) 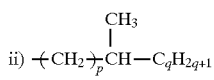

wherein p denotes an integer of 0–5 and q denotes an integer of 2–11 (optically active or inactive);

iii) 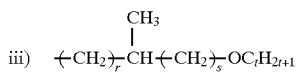

wherein r denotes an integer of 0–6, s denotes 0 or 1, and t denotes an integer of 1–14 (optically active or inactive);

iv) 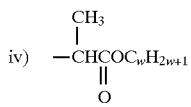

wherein w denotes an integer of 1–15 (optically active or inactive);

v) 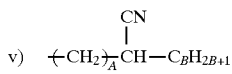

wherein A denotes an integer of 0–2 and B denotes an integer of 1–15 (optically active or inactive); and vi) 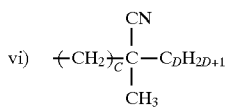

wherein C denotes an integer of 0–2 and D denotes an integer of 1–15 (optically active or inactive).

In formulating the liquid crystal composition according to the present invention, the liquid crystal composition may desirably contain 1–80 wt. %, preferably 1–60 wt. %, more preferably 1–40 wt. % of an optically active compound (mesomorphic compound) represented by the formula (I).

Further, when two or more species of the optically active compounds represented by the formula (I) are used, the liquid crystal composition may desirably contain 1–80 wt. %, preferably 1–60 wt. %, more preferably 1–40 wt. %, of the two or more species of the mesomorphic compounds represented by the formula (I).

The liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer 4 may have a thickness of ordinarily 10 Å–1 micron, preferably 10–3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 μm, preferably 1 to 5 μm.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
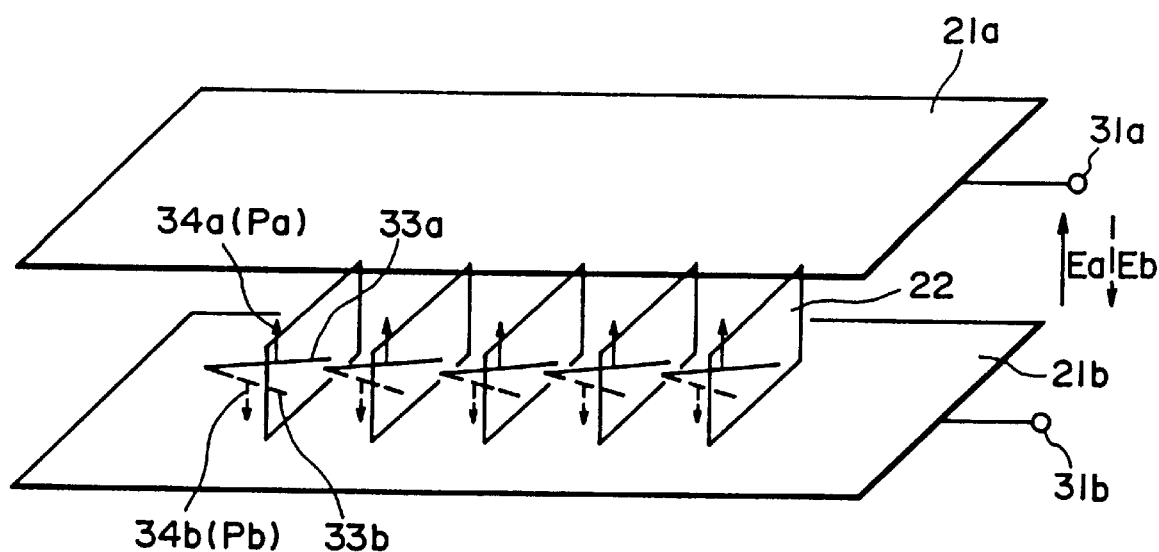

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
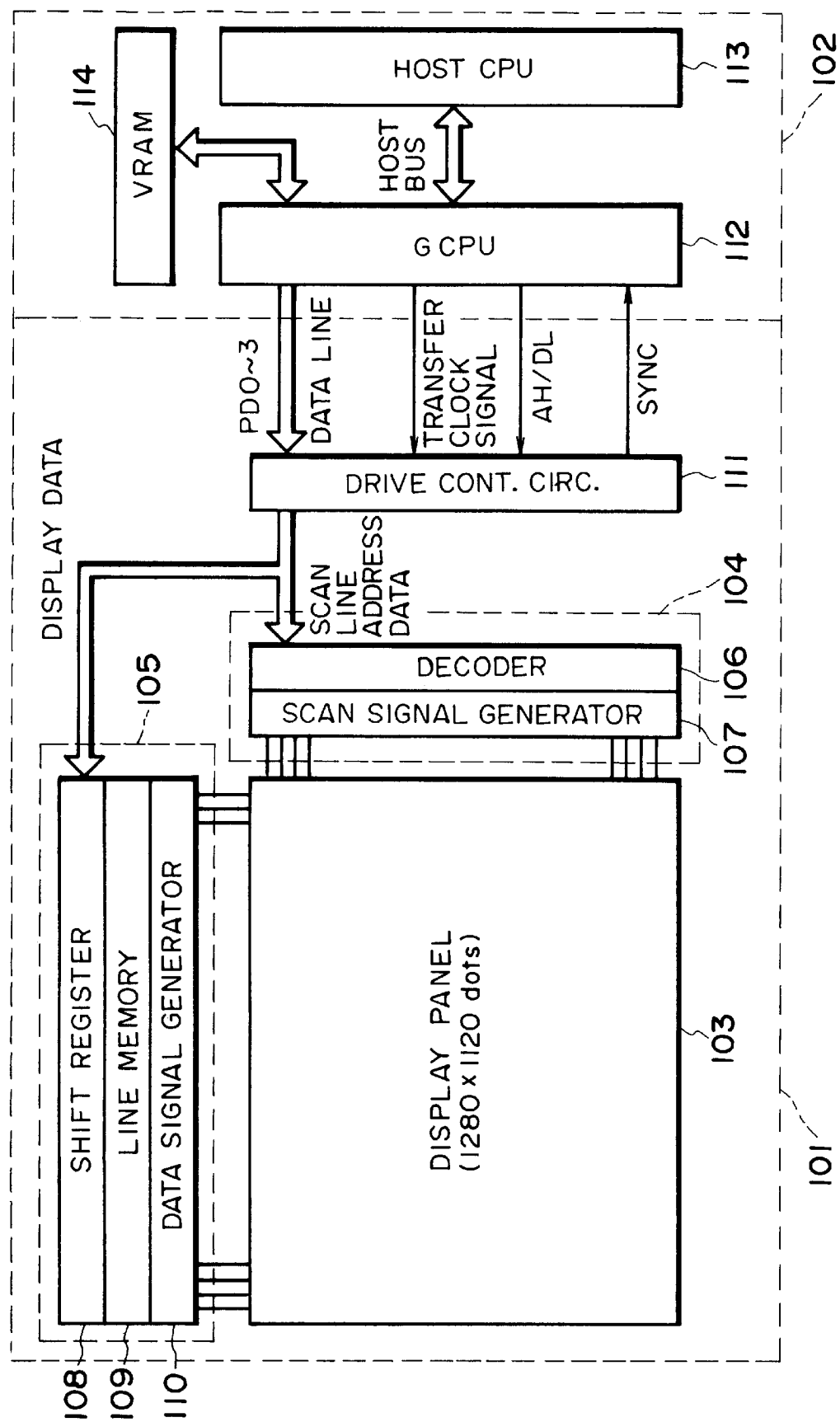
FIG. 4 is a block diagram showing a display apparatus comprising a liquid crystal device utilizing ferroelectricity of a liquid crystal composition and a graphic controller.
Figure 5:
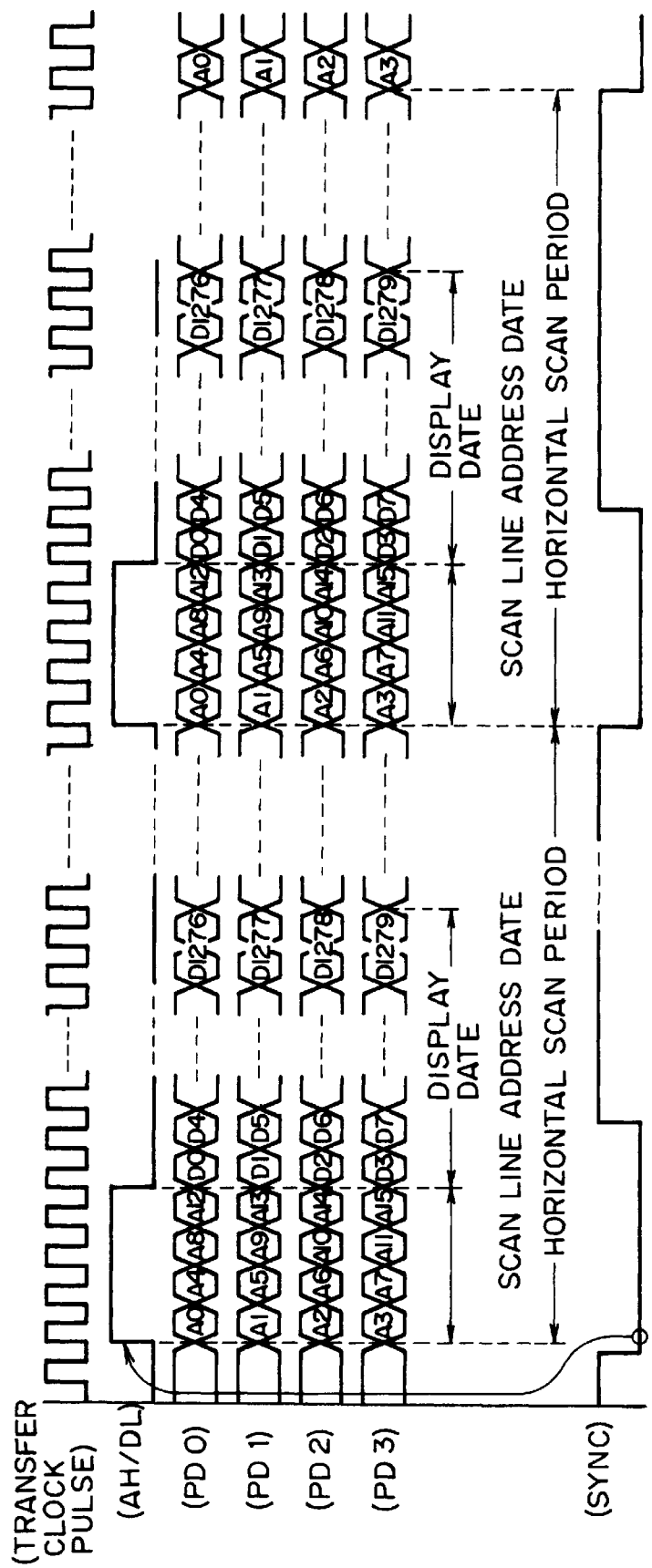
FIG. 5 is a time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel part.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, herein referred to as "GCPU" ) 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically with reference to examples. It is however to be understood that the present invention is not restricted to these examples.

EXAMPLE 1

Production of optically active 5-(3-fluorononyl)-2-(4-decylphenyl)pyrimidine (Example Compound (Ex. Comp.) No. 19)

Optically active 5-(3-fluorononyl)-2-(4-decylphenyl) pyrimidine was synthesized through the following steps 1–10.

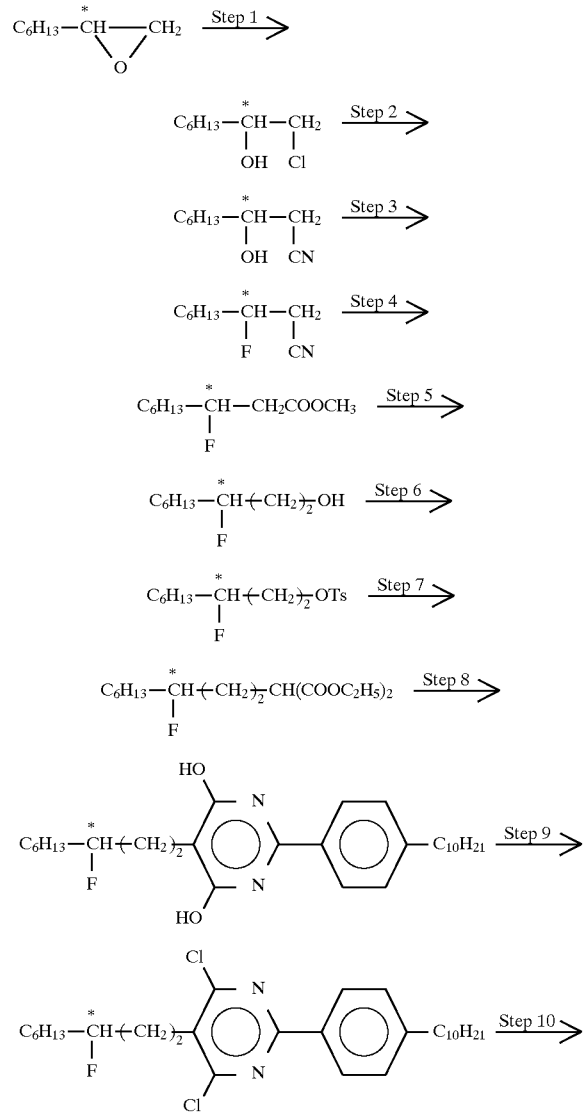

-continued $$C_6H_{13}-\overset{*}{C}H\text{-}(CH_2)_2-\underset{F}{\underset{|}{\phantom{C}}}\bigcirc\hspace{-1em}\underset{N}{\overset{N}{\phantom{\bigcirc}}}-\bigcirc-C_{10}H_{21}$$

Ts: p-toluenesulfonyl group

Step 1 Production of (R)-1-chloro-2-octanol

Under nitrogen atmosphere, 10 g (65.5 mM) of (R)-1,2-epoxyoctane and 100 ml of dry diethyl ether (Et$_2$O) were placed in a 200 ml two-necked round-bottomed flask and cooled on an ice bath. Into the mixture, hydrogen chloride gas was blown, followed by stirring for 2.5 hours. Then, the ice bath was removed and the mixture was further stirred for 2 hours at room temperature. After the reaction, the reaction mixture was poured into 250 ml of ice water and subjected to extraction with diethyl ether. The organic layer was washed with distilled water and dried with anhydrous magnesium sulfate, followed by distilling-off of the solvent to obtain 10.4 g of (R)-1-chloro-2-octanol.

Step 2 Production of 3-hydroxynonanenitrile

Under nitrogen atmosphere, 6.2 g (126 mM) of sodium cyanide and 50 ml of dimethyl sulfoxide (DMSO) were placed in two-necked round-bottomed flask and dissolved by heating, followed by stirring. The solution was left standing and a solution of 10.4 g of (R)-1-chloro2-octanol in 20 ml of DMSO was added dropwise to the solution at 50° C., followed by stirring for 20 hours at 50° C. After the reaction, distilled water was added to the reaction mixture, followed by extraction with diethyl ether. The organic layer was washed with distilled water and dried with anhydrous sodium sulfate, followed by distilling-off of the solvent under reduced pressure to obtain 8.48 g (54.7 mM) of (R)-3-hydroxynonanenitrile.

Yield: 85.4% (on the basis of (R)-1,2-epoxyoctane)
Boiling point: 115°–120° C. (4 Torr)
Specific rotation: $[\alpha]_{435}^{22}$=+24.5 degrees, $[\alpha]_D^{22}$=+12.2 degrees (c=1.12, Et$_2$O)

Step 3 Production of (S)-3-fluorononanenitrile

Under nitrogen atmosphere, 8.0 g (51.6 mM) of (R)-3-hydroxynonanenitrile and 40 ml of dry Et$_2$O were placed in a 200 ml two-necked round-bottomed flask and cooled on an ice bath. To the mixture, a solution of 22 g (51.6 mM) of hexafluoropropenediethylamine in 50 ml of dry Et$_2$O was added dropwise, followed by stirring for 19 hours at room temperature. After the reaction, the reaction mixture was poured into distilled water and subjected to extraction with Et$_2$O. The organic layer was washed with distilled water and dried with anhydrous magnesium sulfate, followed by distilling-off of the solvent and purification by silica gel column chromatography (300 g of silica gel, eluent: hexane/ethyl acetate=20/1) to obtain 4.31 g (27.5 mM) of (S)-3-fluorononanenitrile (Yield: 53.2%).

Specific rotation: $[\alpha]_{435}^{22}$+−16.8 degrees, $[\alpha]_D^{26}$=−9.4 degrees (c=1.20, Et$_2$O)

Step 4 Production of methyl (S)-3-fluorononanoate

Under nitrogen atmosphere, 4.31 g (27.5 mM) of (S)-3-fluorononanenitrile and 9 ml of dry methanol were placed in a flask and cooled on an ice bath. Into the mixture, hydrogen chloride gas was blown, followed by stirring for 1.5 hours. Then, the ice bath was removed and the mixture was further stirred for 16 hours at room temperature. To the resultant mixture, 6 g of distilled water was added, followed by stirring for 3 hours at 60° C. After the reaction, distilled water was added to the reaction mixture, followed by extraction with Et$_2$O. The organic layer was washed with 5 wt. %—sodium hydrogencarbonate aqueous solution and dried with anhydrous magnesium sulfate, followed by distilling-off of the solvent to obtain 5.10 g (26.8 mM) of methyl (S)-3-fluorononanoate (Yield: 97.9%).

Specific rotation: $[\alpha]_{435}^{28}$=−19.2 degrees, $[\alpha]_D^{28}$=−9.9 degrees (c=2.50, Et$_2$O)

In order to measure an optical purity of the above product, (S)-3-fluorononanoic acid was derived from the product and modified into a diastereomer amide in conjunction with (−)-naphthylethylamine. The process of production of the diasterometer amide and the method of measuring an optical purity were described hereinbelow.

Production of (S)-2-fluorononanoic acid $$C_6H_{13}-\overset{*}{C}HCH_2COOCH_3 \longrightarrow C_6H_{13}-\overset{*}{C}HCH_2COOH$$
$$\phantom{C_6H_{13}-}|\phantom{CHCH_2COOCH_3} \phantom{\longrightarrow} \phantom{C_6H_{13}-}|$$
$$\phantom{C_6H_{13}-}F\phantom{CHCH_2COOCH_3} \phantom{\longrightarrow} \phantom{C_6H_{13}-}F$$

In a two-necked round-bottomed flask, 98 mg (0.52 mM) of methyl (S)-3-fluorononanoate and 1 ml of acetic acid were placed. To the mixture, 1 ml of concentrated hydrochloric acid was added, followed by stirring for 4 hours at 90° C. After the reaction, ice water was added to the reaction mixture, followed by extraction with Et$_2$O. The organic layer was sufficiently washed with distilled water and dried with anhydrous magnesium sulfate, followed by distilling-off of the solvent under reduced pressure to obtain 78 mg (0.44 mM) of (S)-3-fluorononanoic acid.

Yield: 85.7%
Boiling point: 100° C. (4 Torr)
Specific ration: $[\alpha]_{435}^{27}$=−22.5 degrees, $[\alpha]_D^{29}$=−12.1 degrees (c=1.44, Et$_2$O)

Measurement of optical purity of 3-fluorononanoic acid $$C_6H_{13}-\overset{*}{C}HCH_2COOH + \underset{\text{(naphthyl)}}{H_2N-\overset{*}{C}H-CH_3} \longrightarrow$$

$$C_6H_{13}-\overset{*}{C}HCH_2\overset{O}{\overset{\|}{C}}NH$$
$$\phantom{C_6H_{13}-}|\phantom{CHCH_2CNH} \phantom{|}$$
$$\phantom{C_6H_{13}-}F \phantom{CHCH_2CNH} *CH-CH_3$$

Under nitrogen atmosphere, 40 mg (0.23 mM) of (S)-3-fluorononanoic acid and 1 ml of dry dichloromethane were placed in a two-necked flask. 27 g (0.22 mM) of N,N-dimethylaminopyridine, 51 mg (0.3 mM) of (−)-naphthylethylamine and 71 mg (0.34 mM) of dicyclohexylcarbodiimide were added to the mixture, followed by stirring for 15 hours at room temperature. The precipitated N,N'-dicyclohexylurea was filtered out, followed by distilling-off of the solvent under reduced pressure and purification by thin-layer chromatography (eluent: hexane/ethyl acetate=2/1, Rf=0.5) to obtain 35 mg (0.11 mM) of a diastereomer amide (Yield: 47.8%).

The thus obtained diastereomer amide was subjected to measurement of optical purity according to high speed liquid chromatography. As a result, (S)-3-fluorononanoic acid showed an optical purity of 92% e.e.

Step 5 Production of (S)-3-fluorononanol

Under nitrogen atmosphere, 1 ml of dry tetrahydrofuran (THF) and 88 mg (2.3 mM) of lithium aluminum hydride were placed in a two-necked round-bottomed flask and cooled on an ice path. To the mixture, a solution of 400 mg (2.1 mM) of methyl (S)-3-fluorononanoate in 1 ml of dry THF was added dropwise. The ice bath was removed and the resultant mixture was stirred for 2 hours at room temperature. After the reaction, the reaction vessel (flask) was cooled on an ice bath. To the resultant reaction mixture, 0.5 ml of saturated sodium sulfate was added, followed by stirring for 30 minutes. To the resultant mixture, 4 ml of 3M-hydrochloric acid (HCl) was added, followed by extraction with Et$_2$O. The organic layer was washed with 5 wt. %-sodium hydrogencarbonate aqueous solution and dried with anhydrous magnesium sulfate, followed by distilling-off of the solvent under reduced pressure to obtain 270 mg (1.66 mM) of (S)-3-fluorononanol.

Yield: 79.0%

Boiling point: 77°–80° C. (5 Torr)

Specific rotation: $[\alpha]_{435}^{22}$=+18.2 degrees, $[\alpha]_D^{22}$=+8.74 degrees (c=1.56, Et$_2$O)

Step 6 Production of (S)-3-fluorononyl p-toluene-sulfonate

Under nitrogen atmosphere, 1.76 g (10.9 mM) (S)-3-fluorononanol and 5 ml of dry dichloromethane were placed in a two-necked flask and cooled on an ice bath. To the mixture, 2.5 g (13.1 mM) of p-toluenesulfonyl chloride and 1.32 g (13.1 mM) of triethylamine were added, followed by stirring for 15 hours at room temperature. After the reaction, 5 ml of 3M-HCl was added to the reaction mixture, followed by extraction with dichloromethane. The organic layer was washed with 1M-HCl and dried with anhydrous magnesium sulfate, followed by distilling-off of the solvent and purification by silica gel column chromatography (100 g of silica gel; eluent: benzene/hexane=2/1; Rf=0.4) to obtain 2.94 g (9.30 mM) of (S)-fluorononyl p-toluenesulfonate (Yield: 85.3%).

Specific rotation: $[\alpha]_{435}^{24}$=+19.0 degrees, $[\alpha]_D^{26}$=+9.4 degrees (c=1.43, Et$_2$O)

Step 7 Production of (S)-2-(3-fluorononyl)malonic diether ester

Under nitrogen atmosphere, 15 ml of dry ethanol was placed in a two-necked round-bottomed flask. To the dry ethanol, 175 mg (7.60 mM) of metal sodium was added and completely dissolved therein. To the solution, 1.52 g (9.50 mM) of diethyl malonate was added and subsequently a solution of 2.00 g (6.33 mM) of (S)-3-fluorononyl p-toluenesulfonate in dry ethanol, followed by heat-refluxing for 5 hours. After the reaction, the reaction mixture was left standing at room temperature and the insoluble matter was filtered out, followed by distilling-off of ethanol under reduced pressure, addition of 4 ml of saturated common salt aqueous solution and extraction with Et$_2$O. The organic layer was washed with saturated common salt aqueous solution and dried with anhydrous magnesium sulfate, followed by distilling-off of the solvent under reduced pressure to obtain 1.28 g (4.20 mM) of (S)-2-(3-fluorononyl) malonic diethyl ether.

Yield: 66.3%

Boiling point: 117°–120° C. (0.15 Torr)

Specific rotation: $[\alpha]_{435}^{23}$=+4.5 degrees, $[\alpha]_D^{24}$=+1.7 degrees (c=1.04, Et$_2$O)

Step 8 Production of (S)-4,6-dihydroxy-5-(3-fluorononyl)-2-(4-decylphenyl)pyrimidine Under nitrogen atmosphere, 3 ml of dry methanol was placed in a two-necked round-bottomed flask. To the methanol, 113 mg (4.92 mM) of metal sodium was added and dissolved therein. To the solution, 584 mg (1.97 mM) of 4-decylbenzamidine hydrochloride was added and stirred for 20 minutes. To the mixture, a solution of 500 mg (1.64 mM) of (S)-2-(3-fluorononyl)malonic diethyl ester in 1 ml of dry methanol was added, followed by stirring for 16 hours at room temperature and distilling-off of methanol under reduced pressure. To the resultant reaction mixture, 4 ml of 6M-HCl was added to precipitate a crystal. The crystal was recovered by filtration and washed with ethanol and Et$_2$O and further dried. The resultant crystal was recrystallized from 2.5 ml of N,N-dimethylformamide (DMF) to obtain 428 mg (0.91 mM) of (S)-4,6-dihydroxy-5-(3-fluorononyl)-2-(4-decylphenyl)pyrimidine (Yield: 55.3%).

Melting point: 237°–239° C. (decomposition)

Step 9 Production of (S)-4,6-dichloro-5-(3-fluorononyl)-2-(4-decylphenyl)pyrimidine 428 mg (0.91 mM) of (S)-4,6-dihydroxy-5-(3-fluorononyl)-2-(4-decylphenyl)pyrimidine, 2.5 ml of phosphorus oxychloride and 455 mg of N,N-diethylaniline were placed in a two-necked round-bottomed flask under nitrogen atmosphere, followed by stirring for 40 hours at 100° C. After the reaction, excessive phosphorus oxychloride was distilled off under reduced pressure. To the resultant reaction mixture, 2M-sodium hydroxide aqueous solution was added to alkalinize the reaction mixture, followed by extraction with Et$_2$O. The organic layer was washed with 3M-HCl and distilled water and dried with anhydrous sodium sulfate, followed by distilling-off of the solvent and purification by silica gel column chromatography (15 g of silica gel; eluent: benzene/hexane=3/1; Rf=0.5) to obtain 372 mg (0.73 mM) of (S)-4,6-dichloro-5-(3-fluorononyl)-2-(4-decylphenyl) pyrimidine (Yield: 80.3%).

Specific rotation: $[\alpha]_{435}^{26}$=+8.9 degrees, $[\alpha]_D^{24}$=+3.3 degrees (c=1.02, Et$_2$O)

Step 10 Production of (S)-5-(3-fluorononyl)-2-(decylphenyl)pyrimidine 72 mg of palladium-carbon (palladium=about 5%), 372 mg (0.73 mM) of (S)-4,6-dichloro-(5-3-fluorononyl)-2-(4-decylphenyl)pyrimidine, 5 ml of 99%-ethanol, 118 mg (2.92 mM) of magnesium oxide and 0.3 ml of distilled water were placed in a two-necked round-bottomed flask and subjected to hydrogen addition for 5 hours at 60° C. After the reaction, benzene was added to the reaction mixture and the catalyst as removed from the reaction mixture, followed by distilling-off of the solvent and purification by thin-layer chromatography (eluent: benzene; Rf=0.5) to obtain 222 mg (0.50 mM) of (S)-5-(3-fluorononyl)-2-(4-decylphenyl) pyrimidine (crude product). The crude product was recrystallized from hexane to obtain an objective product (Yield: 69.2%).

Specific rotation: $[\alpha]_{435}^{24}$=+26.7 degrees, $[\alpha]_D^{26}$=+10.9 degrees (c=1.20, CHCl$_3$)

Phase transition temperature (°C.)

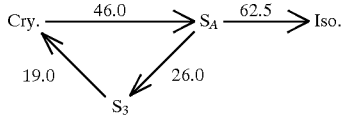

Iso.: isotropic phase
S$_A$: smectic A phase
S$_3$: higher-order smectic phase (un-identified)
Cry.: crystal

EXAMPLE 2

Production of optically active 5-(3-fluorononyl)-2-(4-octylphenyl)pyrimidine (Ex. Comp. No. 21)

Optically active 5-(3-fluorononyl)-2-(4-octylphenyl) pyrimidine was prepared in the same manner as in Example 1 except that 4-octylbenzamidine hydrochloride was used instead of 4-decylbenzamidine hydrochloride used in Step 8 of Example 1.

The reaction scheme, yields and physical properties are shown below.

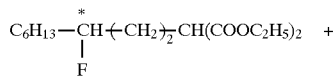

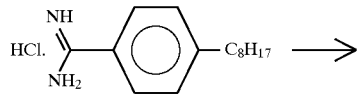

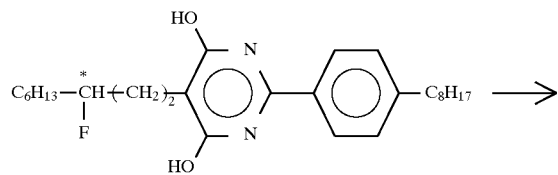

Yield: 46%
Melting point: 240° C. (decomposition)

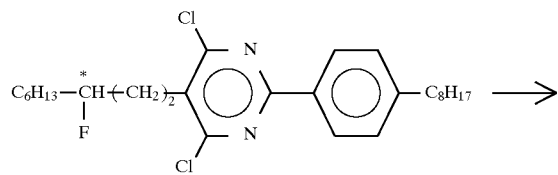

Yield: 59.5%
Specific rotation: $[\alpha]_{435}^{24} = +8.8$ deg.
$[\alpha]_D^{26} = +3.2$ deg.
(c = 0.76, CHCl₃)

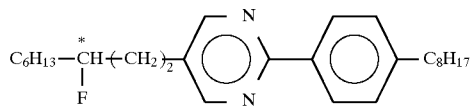

Yield: 51.4%
Specific rotation: $[\alpha]_{435}^{24} = +29.2$ deg.
$[\alpha]_D^{26} = +12.6$ deg.
(c = 0.76, CHCl₃)

Phase transition temperature (°C.)

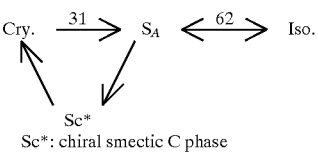

Sc*: chiral smectic C phase

EXAMPLE 3

Production of optically active 5-(3-fluorononyl)-2-[4-(2-fluorodecyloxy)phenyl]pyrimidine (Ex. Comp. No. 15)

Optically active 2-(3-fluorononyl)malonic diethyl ester was prepared in the same manner as in Steps 1–7 of Example 1.

Optically active 5-(3-fluorononyl)-2-[4-(2-fluorodecyloxy)phenyl]pyrimidine was synthesized from the optically active compound through the following reaction scheme including Steps 1–3.

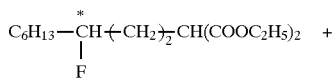

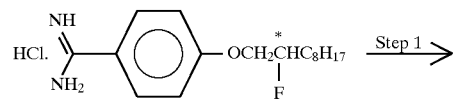

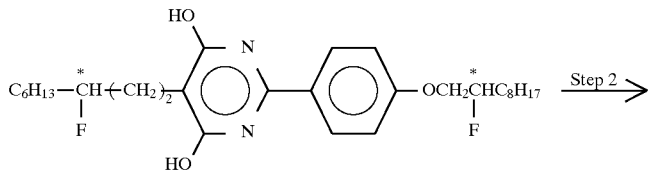

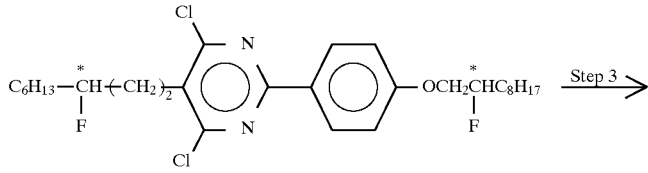

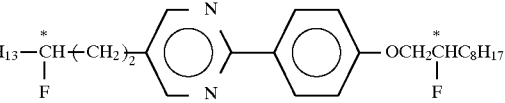

Step 1 Production of 4,6-dihydroxy-5-((3S)-3-fluorononyl)-2-[4-((2S)-2-fluorodecyloxy)phenyl]-pyrimidine Under nitrogen atmosphere, 2.4 ml of dry methanol was placed in a two-necked round-bottomed flask. To the methanol, 90 mg (3.93 mM) of metal sodium was added and dissolved therein. To the solution, 519 mg (1.57 mM) of (S)-4-(2-fluorodecyloxy)benzamidine hydrochloride was added and stirred for 20 minutes. To the mixture, a solution of 400 mg (1.31 mM) of (S)-2-(3-fluorononyl)malonic diethyl ester in 1 ml of dry methanol was added, followed by stirring for 16 hours at room temperature and distilling-off of methanol under reduced pressure. To the resultant reaction mixture, 4 ml of 6M-HCl was added to precipitate a crystal. The crystal was recovered by filtration and washed with ethanol and Et$_2$O and further dried under reduced pressure. The resultant crystal was recrystallized from DMF to obtain 390 mg (0.77 mM) of 4,6-dihydroxy-5-((3S)-3-fluorononyl)-2-[4-((2S)-2-fluorodecyloxy)phenyl]pyrimidine (Yield: 58.8%).

Melting point: 250°–251° C. (decomposition)

Step 2 Production of 4,6-dichloro-5-((3S)-3-fluorononyl)-2-[4-((2S)-2-fluorodecyloxy)phenyl]pyrimidine 390 mg (0.77 mM) of 4,6-dihydroxy-5-((3S)-3-fluorononyl)- 2-[4-((2S)-2-fluorodecyloxy)phenyl]-pyrimidine 2.4 ml of phosphorus oxychloride and 395 mg of N,N-diethylaniline were placed in a two-necked round-bottomed flask under nitrogen atmosphere, followed by stirring for 40 hours at 100° C. After the reaction, excessive phosphorus oxychloride was distilled off under reduced pressure. To the resultant reaction mixture, 2M-sodium hydroxide aqueous solution was added to alkalinize the reaction mixture, followed by extraction with Et$_2$O. The organic layer was washed with 3M-HCl and distilled water and dried with anhydrous sodium sulfate, followed by distilling-off of the solvent and purification by thin-layer chromatography (eluent: benzene/hexane=3/1; Rf=0.5) to obtain 167 mg (0.31 mM) of 4,6-dichloro-5-((3S)-3-fluorononyl)-2-[4-((2S)-2-fluorodecyloxy)phenyl]pyrimidine (Yield: 40.0 %).

Specific rotation: $[\alpha]_{435}^{24}$=+14.8 degrees, $[\alpha]_D^{26}$=+4.7 degrees (c=0.98, CHCl$_3$).

Step 3 Production of 5-((3S)-3-fluorononyl)-2-[4-((2S)-2-fluorodecyloxy)phenyl]pyrimidine 312 mg of palladium-carbon (palladium=about 5%), 167 mg (0.31 mM) of 4,6-dichloro-5-((3S)-3-fluorononyl)-2-[4-((2S)-2-fluorodecyloxy)phenyl]pyrimidine, 4 ml of ethanol, 50 mg (1.24 mM) of magnesium oxide and 0.2 ml of distilled water were placed in a two-necked round-bottomed flask and subjected to hydrogen addition for 5 hours at 60° C. After the reaction, benzene was added to the reaction mixture and the catalyst as removed from the reaction mixture, followed by distilling-off of the solvent and purification by thin-layer chromatography (eluent: benzene; Rf=0.5) to obtain 92 mg (0.19 mM) of 5-((3S)-3-fluorononyl)-2-[4-(2S)-2-fluorodecyloxy)phenyl]pyrimidine (crude product). The crude product was recrystallized from 99%-ethanol to obtain an objective product (Yield: 62.6%).

Specific rotation: $[\alpha]_{435}^{24}$=+30.8 degrees, $[\alpha]_D^{26}$=+13.7 degrees (c=0.92, CHCl$_3$).

Phase transition temperature (°C.)

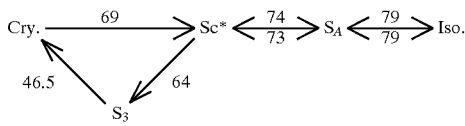

EXAMPLE 4

Production of optically active 5-(3-fluorononyl)-2-(4-decyloxyphenyl)pyrimidine (Ex. Comp. No. 20)

Optically active 5-(3-fluorononyl)-2-(4-decyloxyphenyl) pyrimidine was prepared in the same manner as in Example 3 except that 4-decyloxybenzamidine hydrochloride was used instead of optically active 4-(2-fluorodecyloxy) benzamidine hydrochloride used in Step 1 of Example 3.

The reaction scheme, yields and phase transition series are shown below.

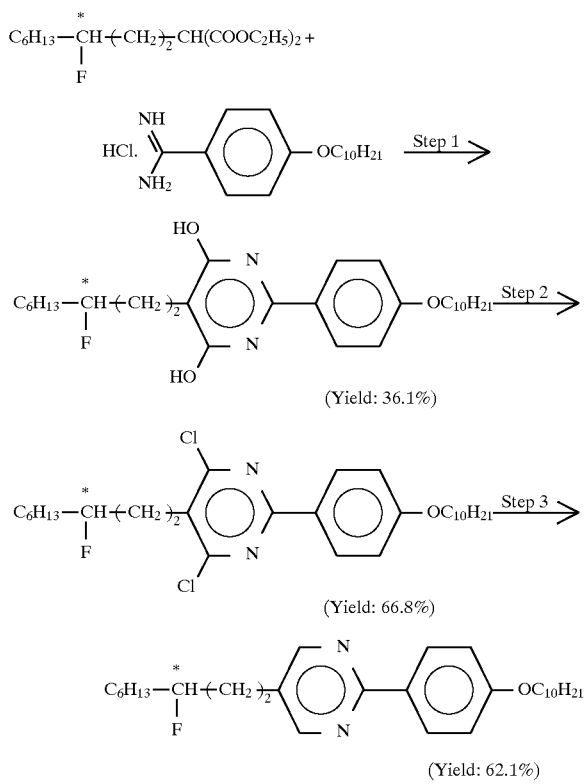

Phase transition temperature (°C.)

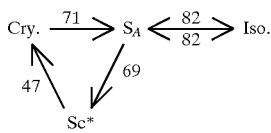

EXAMPLE 5

A liquid crystal composition A was prepared by mixing the following compounds including the compound (Ex. Comp. No. 19) prepared in Example 1 in the respectively indicated proportions.

| Structural formula | wt. parts |
|---|---|
| 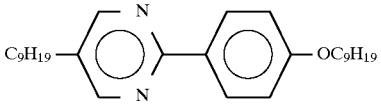 C₉H₁₉—[pyrimidine]—[phenyl]—OC₉H₁₉ | 25.5 |
| 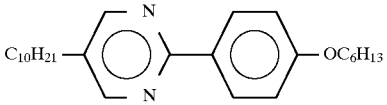 C₁₀H₂₁—[pyrimidine]—[phenyl]—OC₆H₁₃ | 25.5 |
| 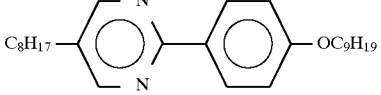 C₈H₁₇—[pyrimidine]—[phenyl]—OC₉H₁₉ | 25.5 |
| 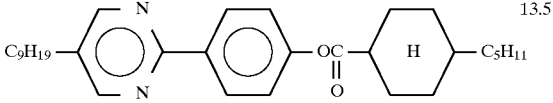 C₉H₁₉—[pyrimidine]—[phenyl]—OC(=O)—[cyclohexyl-H]—C₅H₁₁ | 13.5 |
| 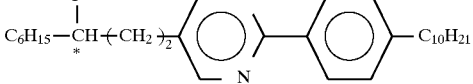 C₆H₁₅—CHF—(CH₂)₂—[pyrimidine]—[phenyl]—C₁₀H₂₁ (Ex. Comp. No. 19) | 10.0 |

The liquid crystal composition A showed the following phase transition series.

Phase transition temperature (°C.)

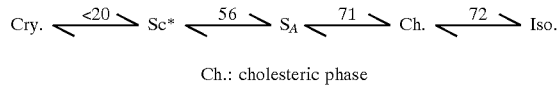

Ch.: cholesteric phase

EXAMPLE 6

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 seconds and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell.

Then, the liquid crystal composition A prepared in Example 5 was heated into an isotropic liquid, and injected into the above prepared cell under vacuum and, after sealing, was gradually cooled to 25° C. at a rate of 20° C./hour to prepare a ferroelectric liquid crystal device. The cell gap was found to be about 2 microns as measured by a Berek compensator.

The ferroelectric liquid crystal device was subjected to measurement of the magnitude of spontaneous polarization Ps and an optical response time (time from voltage application until the transmittance change reaches 90% of the maximum under the application of a peak-to-peak voltage Vpp of 10 V in combination with right-angle cross-nicol polarizers).

The results are shown below.

| | 25° C. | 30° C. | 45° C. |
|---|---|---|---|
| Response time (μsec) | 200 | 190 | 160 |
| Ps (nC/cm²) | −4.3 | −3.8 | −3.0 |

EXAMPLE 7

A ferroelectric liquid crystal device was prepared in the same manner as in Example 6 except that optically active 5-(3-fluorononyl)-2-[4-(2-fluorodecyloxy)phenyl]pyrimidine prepared in Example 3 was injected into a blank cell and subjected to measurement of Ps in the same manner as in Example 6, whereby the following results were obtained.

| | 65° C. | 70° C. |
|---|---|---|
| Ps (nC/cm²) | −223 | −111 |

EXAMPLE 8

A ferroelectric liquid crystal device was prepared in the same manner as in Example 6 except that optically active 5-(3-fluorononyl)-2-(4-decyloxyphenyl)pyrimidine prepared in Example 4 was injected into a blank cell and subjected to measurement of Ps in the same manner as in Example 6, whereby the following results were obtained.

| | 59° C. | 64° C. |
|---|---|---|
| Ps (nC/cm²) | −51 | −32 |

EXAMPLE 9

A liquid crystal composition B was prepared by mixing the following compounds including the compound (Ex. Comp. No. 15) prepared in Example 3 in the respectively indicated proportions.

| Structural formula | wt. parts |
|---|---|
| 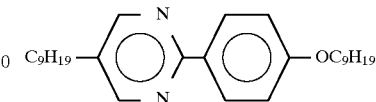 C₉H₁₉—[pyrimidine]—[phenyl]—OC₉H₁₉ | 25.5 |
| 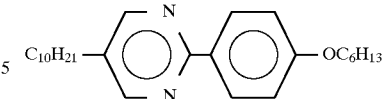 C₁₀H₂₁—[pyrimidine]—[phenyl]—OC₆H₁₃ | 25.5 |

51
-continued

| Structural formula | wt. parts |
|---|---|
| 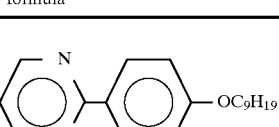 (Ex. Comp. No. 15) | 25.5<br>13.5<br>10.0 |

The liquid crystal composition B showed the following phase transition series.

Phase transition temperature (°C.)

$$\text{Cry.} \xrightarrow{<20} \text{Sc*} \xrightarrow{61} S_A \xrightarrow{71} \text{Ch.} \xrightarrow{75} \text{Iso.}$$

EXAMPLE 10

A ferroelectric liquid crystal device was prepared in the same manner as in Example 6 except that the liquid crystal composition B prepared in Example 9 was injected into a blank cell and subjected to measurement of response time and Ps in the same manner as in Example 6, whereby the following results were obtained.

|  | 25° C. | 30° C. | 40° C. | 50° C. |
|---|---|---|---|---|
| Response time (μsec) | 40 | 38 | 38 | 38 |
| Ps (nC/cm²) | −18.6 | −18.9 | −13.4 | −8.7 |

EXAMPLE 11

A liquid crystal composition C was prepared by mixing the following compounds including the compound (Ex. Comp. No. 20) prepared in Example 4 in the respectively indicated proportions.

| Structural formula | wt. parts |
|---|---|
|  | 25.5 |
|  | 25.5 |

52
-continued

| Structural formula | wt. parts |
|---|---|
| 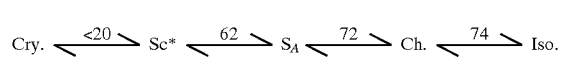 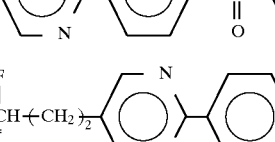 (Ex. Comp. No. 20) | 25.5<br>13.5<br>10.0 |

The liquid crystal composition C showed the following phase transition series.

Phase transition temperature (°C.)

$$\text{Cry.} \xrightarrow{<20} \text{Sc*} \xrightarrow{62} S_A \xrightarrow{72} \text{Ch.} \xrightarrow{74} \text{Iso.}$$

EXAMPLE 12

A ferroelectric liquid crystal device was prepared in the same manner as in Example 6 except that the liquid crystal composition C prepared in Example 11 was injected into a blank cell and subjected to measurement of response time and Ps in the same manner as in Example 6, whereby the following results were obtained.

|  | 25° C. | 30° C. | 40° C. |
|---|---|---|---|
| Response time (μsec) | 92 | 80 | 66 |
| Ps (nC/cm²) | −6.7 | −6.0 | −4.7 |

EXAMPLE 13

A liquid crystal composition D was prepared by mixing the following compounds including the compound (Ex. Comp. No. 29) in the respectively indicated proportions.

| Structural formula | wt. parts |
|---|---|
| (C₉H₁₉— pyrimidine —OC₉H₁₉) | 25.5 |
| (C₁₀H₂₁— pyrimidine —OC₆H₁₃) | 25.5 |
| (C₈H₁₇— pyrimidine —OC₉H₁₉) | 25.5 |

| Structural formula | wt. parts |
|---|---|
| C$_9$H$_{19}$–[pyrimidine]–[phenyl]–OC(=O)–[cyclohexyl H]–C$_5$H$_{11}$ | 13.5 |
| C$_7$H$_{15}$–CH(F)*–(CH$_2$)$_2$–[pyrimidine]–[phenyl]–[phenyl]–C$_6$H$_{13}$ | 10.0 |

(Ex. Comp. No. 29)

A ferroelectric liquid crystal device was prepared in the same manner as in Example 6 except that the liquid crystal composition D was injected into a blank cell and subjected to measurement of response time in the same manner as in Example 6, whereby the following results were obtained.

|  | 30° C. | 40° C. |
|---|---|---|
| Response time ($\mu$sec) | 230 | 220 |

EXAMPLE 14

A liquid crystal composition E was prepared by mixing the following compounds including the compound (Ex. Comp. No. 33) in the respectively indicated proportions.

| Structural formula | wt. parts |
|---|---|
| C$_9$H$_{19}$–[pyrimidine]–[phenyl]–OC$_9$H$_{19}$ | 25.5 |
| C$_{10}$H$_{21}$–[pyrimidine]–[phenyl]–OC$_6$H$_{13}$ | 25.5 |
| C$_8$H$_{17}$–[pyrimidine]–[phenyl]–OC$_9$H$_{19}$ | 25.5 |
| C$_9$H$_{19}$–[pyrimidine]–[phenyl]–OC(=O)–[cyclohexyl H]–C$_5$H$_{11}$ | 13.5 |
| C$_6$H$_{13}$–CH(F)*–(CH$_2$)$_2$–[pyrimidine]–[phenyl]–OC(=O)–[thiophene S]–C$_4$H$_9$ | 10.0 |

(Ex. Comp. No. 33)

A ferroelectric liquid crystal device was prepared in the same manner as in Example 6 except that the liquid crystal composition E was injected into a blank cell and subjected to measurement of response time in the same manner as in Example 6, whereby the following results were obtained.

|  | 30° C. | 40° C. |
|---|---|---|
| Response time ($\mu$sec) | 253 | 241 |

EXAMPLE 15

A liquid crystal composition F was prepared by mixing the following compounds including the compound (Ex. Comp. No. 42) in the respectively indicated proportions.

| Structural formula | wt. parts |
|---|---|
| C$_9$H$_{19}$–[pyrimidine]–[phenyl]–OC$_9$H$_{19}$ | 25.5 |
| C$_{10}$H$_{21}$–[pyrimidine]–[phenyl]–OC$_6$H$_{13}$ | 25.5 |
| C$_8$H$_{17}$–[pyrimidine]–[phenyl]–OC$_9$H$_{19}$ | 25.5 |
| C$_9$H$_{19}$–[pyrimidine]–[phenyl]–OC(=O)–[cyclohexyl H]–C$_5$H$_{11}$ | 13.5 |
| C$_6$H$_{13}$–CH(F)*–(CH$_2$)$_2$–[pyrimidine]–[phenyl(F)]–C$_9$H$_{19}$ | 10.0 |

(Ex. Comp. No. 42)

A ferroelectric liquid crystal device was prepared in the same manner as in Example 6 except that the liquid crystal composition F was injected into a blank cell and subjected to measurement of response time in the same manner as in Example 6, whereby the following results were obtained.

|  | 30° C. | 40° C. |
|---|---|---|
| Response time ($\mu$sec) | 211 | 205 |

EXAMPLE 16

A liquid crystal composition G was prepared by mixing the following compounds including the compound (Ex. Comp. No. 26) in the respectively indicated proportions.

| Structural formula | wt. parts |
|---|---|
| 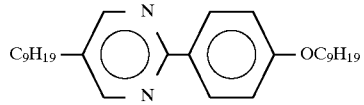 | 25.5 |
| 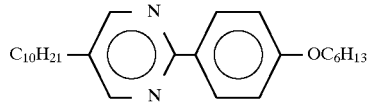 | 25.5 |
| 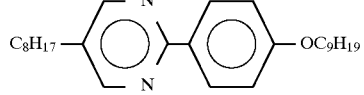 | 25.5 |
| 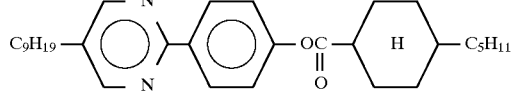 | 13.5 |
| 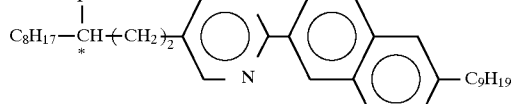 | 10.0 |

(Ex. Comp. No. 26)

A ferroelectric liquid crystal device was prepared in the same manner as in Example 6 except that the liquid crystal composition G was injected into a blank cell and subjected to measurement of response time in the same manner as in Example 6, whereby the following results were obtained.

|  | 30° C. | 40° C. |
|---|---|---|
| Response time (μsec) | 185 | 193 |

As described hereinabove, according to the present invention, there is provided an optically active compound of the formula (I) which can effectively be applied to a liquid crystal device utilizing ferroelectricity when the compound per se assumes a chiral smectic phase. Further, there is also provided a liquid crystal composition containing the compound and assuming a chiral smectic phase, whereby a liquid crystal device comprising the composition can be operated by utilizing ferroelectricity of the composition. The present invention provides a liquid crystal device using such a composition which shows a good switching characteristic and high speed responsiveness.

The present invention further provides a display apparatus and a display method which employ the above-mentioned devices as a display unit (e.g., display panel), whereby good display characteristics can be obtained in combination with a light source, a drive circuit, etc.

What is claimed is:
1. An optically active compound represented by the following formula (I):

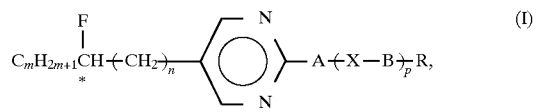

wherein R denotes a linear or branched alkyl group having 1–18 carbon atoms capable of including one or non-neighboring two or more methylene groups which can be replaced with —O—, —S—, —CO—, —COO—, —OCO—, —CH=CH— or —C≡C—, said alkyl group capable of including hydrogen which can be replaced with fluorine; X denotes a single bond, —COO—, —OCO—, —CH$_2$O—, —OCH$_2$—, —CH$_2$CH$_2$— or —C≡C—; A denotes

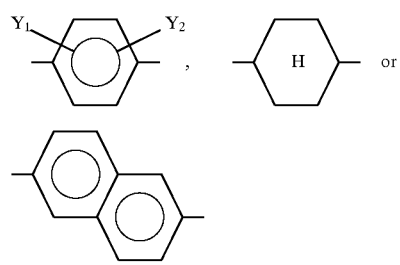

wherein $Y_1$ and $Y_2$ independently denote hydrogen, fluorine, methyl or trifluoromethyl; B denotes A,

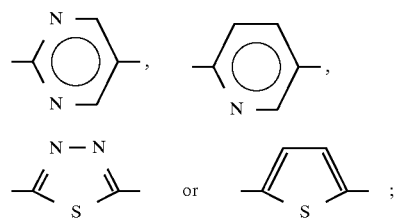

m is an integer of 1–16; n is an integer of 1–6; p is 0 or 1; and * denotes the location of an optically active center, with the proviso that A is

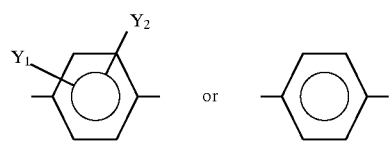

when X is a single bond, B is

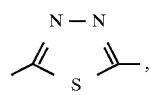

and p is 1.

2. A compound according to claim 1, wherein A in the formula (I) is

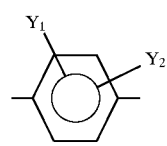

wherein $Y_1$ and $Y_2$ independently denote hydrogen, fluorine, methyl or trifluoromethyl.

3. A compound according to claim 1, which is represented by the following formula (Ia) or (Ib):

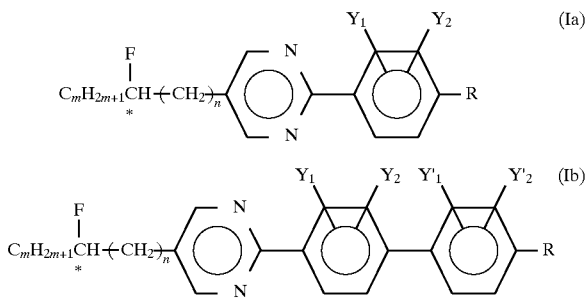

wherein $Y'_1$ and $Y'_2$ independently denote hydrogen, fluorine, methyl or trifluoromethyl; and R, m, n, $Y_1$, $Y_2$ and * have the same meanings as defined above.

4. A compound according to any one of claims 1–3, wherein n in the formula (I) is 2.

5. A compound according to any one of claim 4, wherein R in the formula (I) is any one of the following groups (i) to (v):

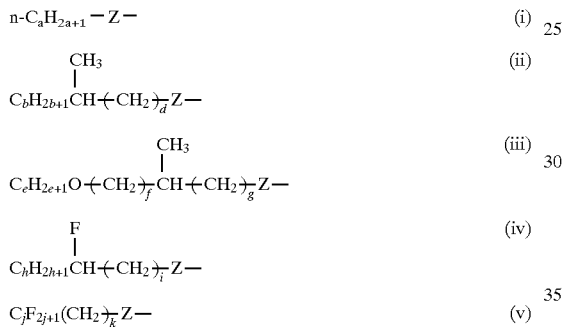

wherein a and j independently denote an integer of 1–16; b and e independently denote an integer of 1–8; f and i independently denote 0 or 1; d, g and k independently denote an integer of 0–7; h is an integer of 1–15; and Z is a single bond, —O—, —COO— or —OCO—.

6. A liquid crystal composition comprising at least two compounds, at least one of which is an optically active compound of the formula (I) according to claim 1.

7. A composition according to claim 6, which comprises 1–80 wt. % of an optically active compound of the formula (I).

8. A composition according to claim 6, which comprises 1–60 wt. % of an optically active compound of the formula (I).

9. A composition according to claim 6, which comprises 1–40 wt. % of an optically active compound of the formula (I).

10. A composition according to claim 6, which has a chiral smectic phase.

11. A composition according to claim 6, which has a cholesteric phase.

12. A liquid crystal device, comprising a pair of electrode plates and a liquid crystal composition according to claim 6 disposed between the electrode plates.

13. A device according to claim 12, which further comprises an alignment control layer.

14. A device according to claim 13, wherein the alignment control layer has been subjected to rubbing.

15. A device according to claim 12, wherein the liquid crystal composition is disposed in a thickness suppressing formation of a helical structure of liquid crystal molecules between the electrode plates.

16. A display apparatus comprising a liquid crystal device according to claim 12, and voltage application means for driving the liquid crystal device.

17. A display apparatus according to claim 16, wherein switching of liquid crystal molecules is performed by utilizing ferroelectricity of the liquid crystal composition to effect display.

18. A display apparatus according to claim 16, which further comprises a light source.

19. A display method, comprising:
providing a liquid crystal composition comprising at least two compounds, at least one of which is an optically active compound of the formula (I) according to claim 1; and
switching the alignment direction of liquid crystal molecules by applying voltages to the liquid crystal composition to effect display.

20. A display method, comprising:
providing a liquid crystal composition comprising at least two compounds, at least one of which is a mesomorphic compound of the formula (I) according to claim 2; and
switching the alignment direction of liquid crystal molecules by applying voltages to the liquid crystal composition to effect display.

21. A display method, comprising:
providing a liquid crystal composition comprising at least two compounds, at least one of which is a mesomorphic compound of the formula (I) according to claim 3; and
switching the alignment direction of liquid crystal molecules by applying voltages to the liquid crystal composition to effect display.

22. A display method, comprising:
providing a liquid crystal composition comprising at least two compounds, at least one of which is a mesomorphic compound of the formula (I) according to claim 4; and
switching the alignment direction of liquid crystal molecules by applying voltages to the liquid crystal composition to effect display.

23. A display method, comprising:
providing a liquid crystal composition comprising at least two compounds, at least one of which is a mesomorphic compound of the formula (I) according to claim 5; and
switching the alignment direction of liquid crystal molecules by applying voltages to the liquid crystal composition to effect display.

24. A method according to claim 19, wherein the liquid crystal composition comprises 1–80 wt. % of an optically active compound of the formula (I).

25. A method according to claim 19, wherein the liquid crystal composition comprises 1–60 wt. % of an optically active compound of the formula (I).

26. A method according to claim 19, wherein the liquid crystal composition comprises 1–40 wt. % of an optically active compound of the formula (I).

27. A method according to claim 19, wherein the liquid crystal composition has a chiral smectic phase.

28. A method according to claim 19, wherein the liquid crystal composition has a cholesteric phase.

29. A display method, comprising:

providing a liquid crystal device comprising a pair of electrode plates and a liquid crystal composition disposed therebetween comprising at least two compounds, at least one of which is a mesomorphic compound of the formula (I) according to claim 1; and switching the alignment direction of liquid crystal molecules by applying voltages to the liquid crystal composition disposed between the electrode plates to effect display.

30. A method according to claim 29, which further comprises an alignment control layer.

31. A method according to claim 30, wherein the insulating alignment control layer has been subjected to rubbing.

32. A method according to claim 29, wherein the liquid crystal composition is disposed in a thickness suppressing formation of a helical structure of liquid crystal molecules between the electrode plates.

* * * * *

UNITED STATES PATENT AND TRADEMARK OFFICE
CERTIFICATE OF CORRECTION

PATENT NO. : 5,830,386
DATED : November 3, 1998
INVENTOR(S) : HIROYUKI NOHIRA ET AL.

It is certified that error appears in the above-identified patent and that said Letters Patent is hereby corrected as shown below:

COLUMN 4

Line 40, "views" should read --views of--.

COLUMN 17

Reaction Schemes:

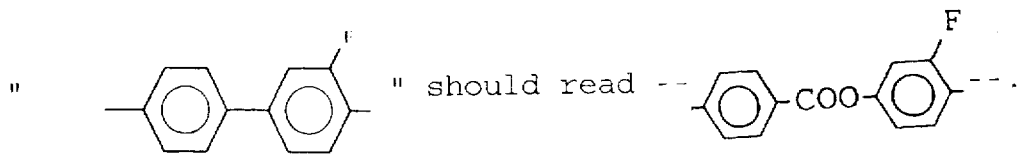

Line 55, "YΔ" should read --Y"--.

COLUMN 21

Line 8, "Y'$_3$" should read --Y$_3$"--.

COLUMN 28

Line 57, "20" should be deleted.

COLUMN 31

Line 60, "—CH 20—or" should read --CH$_2$O— or--.

UNITED STATES PATENT AND TRADEMARK OFFICE
CERTIFICATE OF CORRECTION

PATENT NO. : 5,830,386
DATED : November 3, 1998
INVENTOR(S) : HIROYUKI NOHIRA ET AL.

Page 2 of 3

It is certified that error appears in the above-identified patent and that said Letters Patent is hereby corrected as shown below:

COLUMN 37

Line 8, Close up left margin.
    Line 23, Close up left margin.
    Line 30, Close up left margin.
    Line 38, Close up left margin.

COLUMN 41

Line 54, "$[\alpha]_{435}^{22}+-16.8$ degrees," should read --$[\alpha]_{435}^{22}=-16.8$ degrees,

COLUMN 47

Line 27, "2.4 ml" should read --2.5 ml--.

COLUMN 50

Line 23, "[4-(2-fluorodecyloxy)phenyl]pyrimidin" should read --[4-(2-fluorodecyloxy)phenyl]pyrimidine--.
    Line 24, "e" should be deleted.

UNITED STATES PATENT AND TRADEMARK OFFICE
CERTIFICATE OF CORRECTION

PATENT NO. : 5,830,386
DATED : November 3, 1998
INVENTOR(S) : HIROYUKI NOHIRA ET AL.

It is certified that error appears in the above-identified patent and that said Letters Patent is hereby corrected as shown below:

COLUMN 56

Line 45,

" 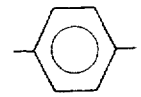 " should read --  --.

Line 39, "1" should read --1,--.
Line 40, "; and" should read --and--.

Signed and Sealed this

Seventh Day of September, 1999

Attest:

Q. TODD DICKINSON

Attesting Officer

Acting Commissioner of Patents and Trademarks